(12) United States Patent
van Rijn et al.

(10) Patent No.: US 11,767,505 B2
(45) Date of Patent: Sep. 26, 2023

(54) BIOMATERIAL SUBSTRATES, CELL CULTURE SYSTEMS COMPRISING THE SAME AND USES THEREOF IN CELL SCREENING APPLICATIONS

(71) Applicants: Rijksuniversiteit Groningen, Groningen (NL); Academisch Ziekenhuis Groningen, Groningen (NL)

(72) Inventors: Patrick van Rijn, Groningen (NL); Martin Conrad Harmsen, Groningen (NL); Qihui Zhou, Groningen (NL); Philipp Till Kuhn, Groningen (NL); Gabriel Liguori, Groningen (NL)

(73) Assignees: RIJKSUNIVERSITEIT GRONINGEN, Groningen (NL); ACADEMISCH ZIEKENHUIS GRONINGEN, Groningen (NL)

(*) Notice: Subject to any disclaimer, the term of this patent is extended or adjusted under 35 U.S.C. 154(b) by 226 days.

(21) Appl. No.: 16/488,397

(22) PCT Filed: Feb. 23, 2018

(86) PCT No.: PCT/NL2018/050118
§ 371 (c)(1),
(2) Date: Aug. 23, 2019

(87) PCT Pub. No.: WO2018/156023
PCT Pub. Date: Aug. 30, 2018

(65) Prior Publication Data
US 2021/0130770 A1    May 6, 2021

(30) Foreign Application Priority Data
Feb. 24, 2017 (EP) .................... 17157897

(51) Int. Cl.
*C12N 5/00* (2006.01)
(52) U.S. Cl.
CPC ........ *C12N 5/0068* (2013.01); *C12N 2533/14* (2013.01); *C12N 2533/30* (2013.01); *C12N 2533/40* (2013.01); *C12N 2535/00* (2013.01)
(58) Field of Classification Search
CPC ............ C12N 2533/30; C12N 2533/40; C12N 2535/00; C12N 5/0068
See application file for complete search history.

(56) References Cited
U.S. PATENT DOCUMENTS
2015/0105323 A1   4/2015 Novak et al.

OTHER PUBLICATIONS

Garcia et al. Generation of stable orthogonal gradients of chemical concentration and substrate stiffness in a microfluidic device. Lab Chip, 2015, 15, 2606-2614 (Year: 2015).*
Schaap-Oziemlak et al. Biomaterial-stem cell interactions and their impact on stem cell response. RSC Adv., 2014, 4, 53307-53320 (Year: 2014).*
Hale et al. Cell Migration at the Interface of a Dual Chemical-Mechanical Gradient. Applied Materials & Interfaces. vol. 2, No. 8, p. 2317-2324 (Year: 2010).*
Almodovar et al. Gradients of physical and biochemical cues on polyelectrolyte multilayer films generated via microfluidics. Lab Chip, 2013, 13, 1562-1570 (Year: 2013).*
Yang et al., "A High-Throughput Assay of Cell-Surface Interactions using Topographical and Chemical Gradients", Advanced Materials, 2009, vol. 21, No. 3, pp. 300-304.
Bhat et al., "Orthogonal Surface-Grafted Polymer Gradients: A Versatile Combinatorial Platform", Journal of Polymer Science: Part B: Polymer Physics, 2005, vol. 43, No. 23, pp. 3384-3394.
Wang et al., "Screening of rat mesenchymal stem cell behaviour on polydimethylsiloxane stiffness gradients", Acta Biomaterialia, 2012, vol. 8, No. 2, pp. 519-530.
Lee et al., "Interaction of Different Types of Cells on Polymer Surfaces with Wettability Gradient", Journal of Colloid and Interface Science, 1998, vol. 205, pp. 323-330.
Kuhn et al., "Double linear Gradient Biointerfaces for Determining Two Parameter Dependent Stem Cell Behavior", ChemNanoMat, 2016, vol. 2, No. 5, pp. 407-413.
Zhou et al., "Directional nanotopographic gradients: a high-throughput screening platform for cell contact guidance", Scientific Reports, 2015, vol. 5, No. 1, pp. 1-12.
Wu et al., "Gradient biomaterials and their influences on cell migration", Interface Focus, 2012, vol. 2, No. 3, pp. 337-355.
Tse et al., "Stiffness Gradients Mimicking In Vivo Tissue Variation Regulate Mesenchymal Stem Cell Fate", PLOS One, 2011, vol. 6, No. 1, e 15978, pp. 1-9.
Keenan et al., "Biomolecular gradients in cell culture systems", Lab on a Chip, 2008, vol. 8, No. 1, pp. 1-44.
Discher et al., "Tissue Cells Feel and Respond to the Stiffness of Their Substrate", Science, 2005, vol. 310, No. 5751, pp. 1139-1143.
Clements et al., "Electrochemistry-enabled fabrication of orthogonal nanotopography and surface chemistry gradients for high-throughput screening", Lab on a Chip, 2012, vol. 12, No. 8, pp. 1480-1486.
International Search Report and Written Opinion for Corresponding International Application No. PCT/NL2018/050118 (10 Pages) (dated May 18, 2018).

* cited by examiner

*Primary Examiner* — Taeyoon Kim
(74) *Attorney, Agent, or Firm* — Lucas & Mercanti, LLP

(57) ABSTRACT

The invention relates to the fields of biomaterials, tissue engineering and regenerative medicine. More specifically, it relates to biomaterial substrates having precise surface properties and the use thereof to investigate cell-material interactions. Provided is a cell culture system having a biomaterial substrate which has at least a first linear surface gradient oriented orthogonally to a second linear surface gradient, wherein the first gradient and the second gradient are selected from the group consisting of stiffness (S), (aligned) topography (T) and wettability (W). Also provided is a cell screening platform having a combination of at least two, preferably at least three, more preferably four distinct cell culture systems.

17 Claims, 21 Drawing Sheets

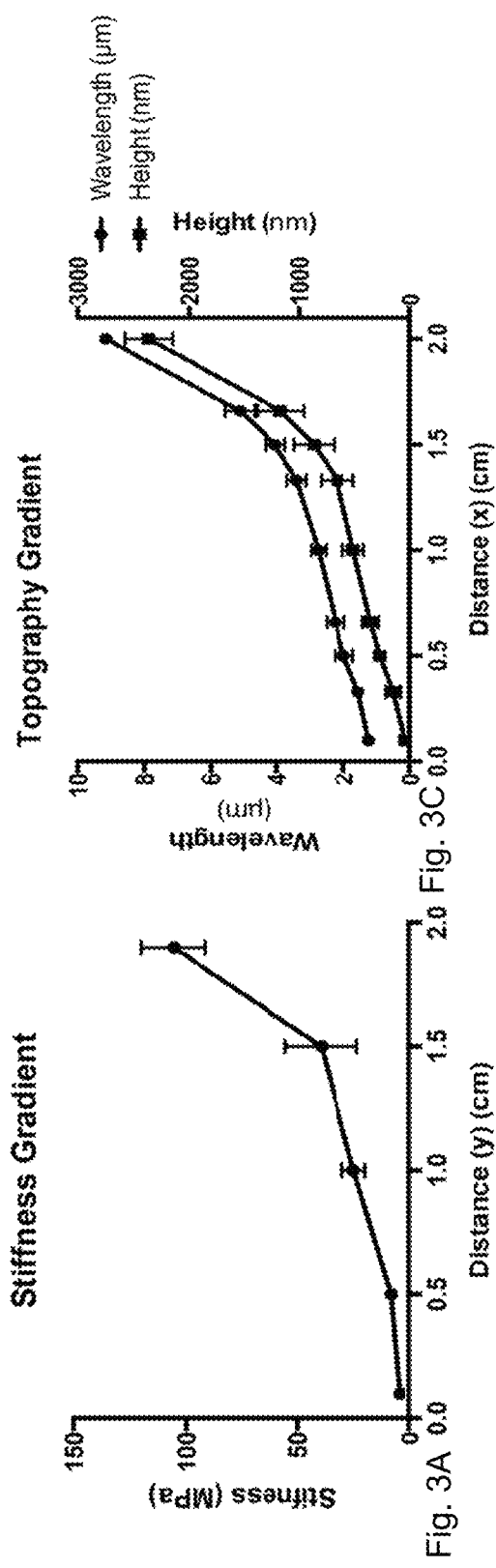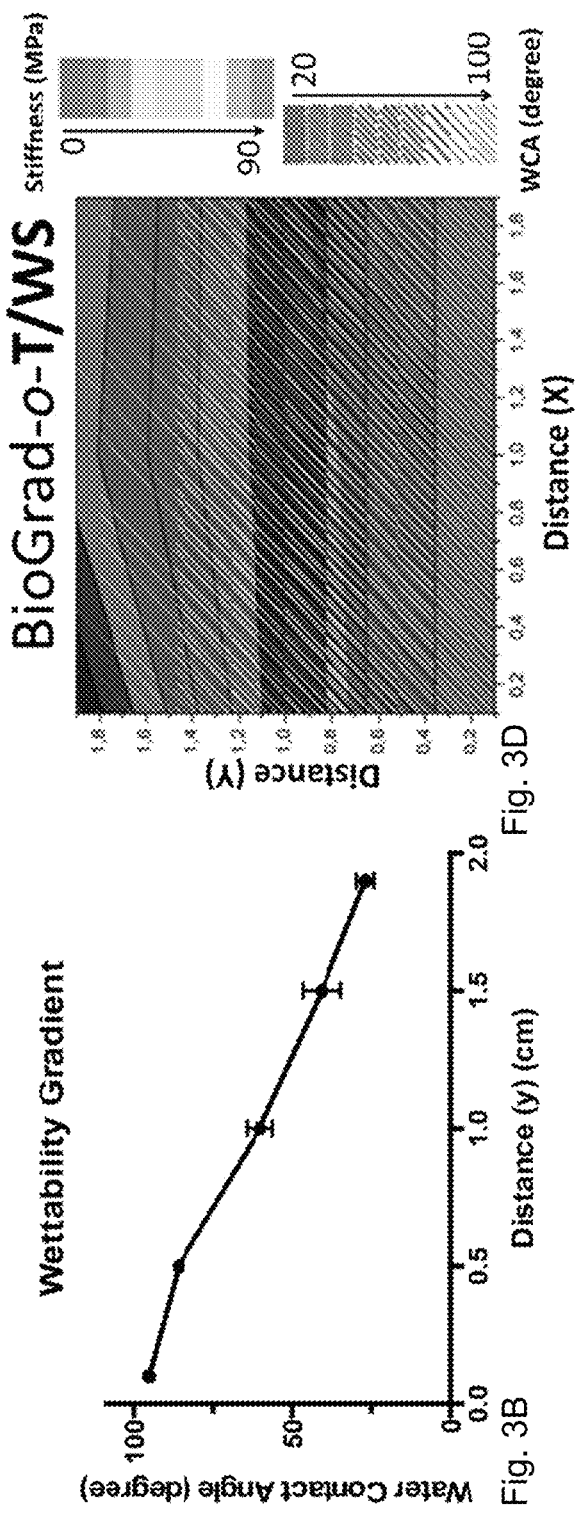
Fig. 3A  Fig. 3B  Fig. 3C  Fig. 3D

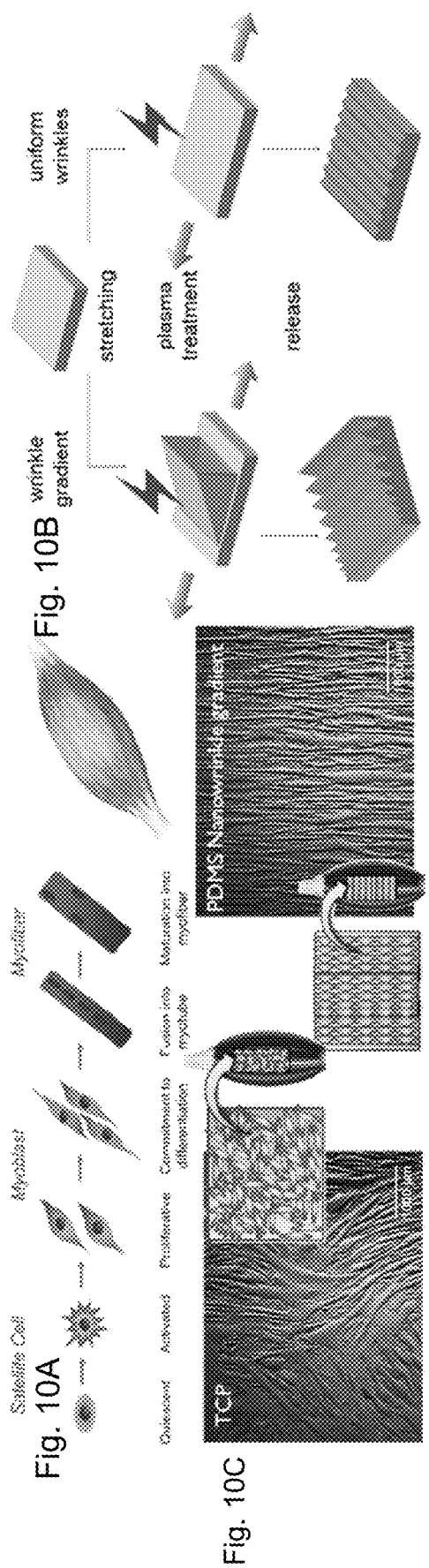

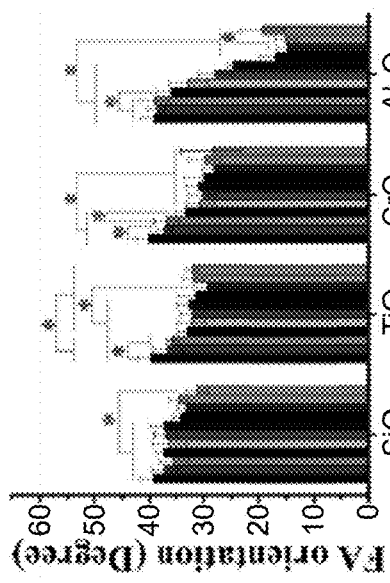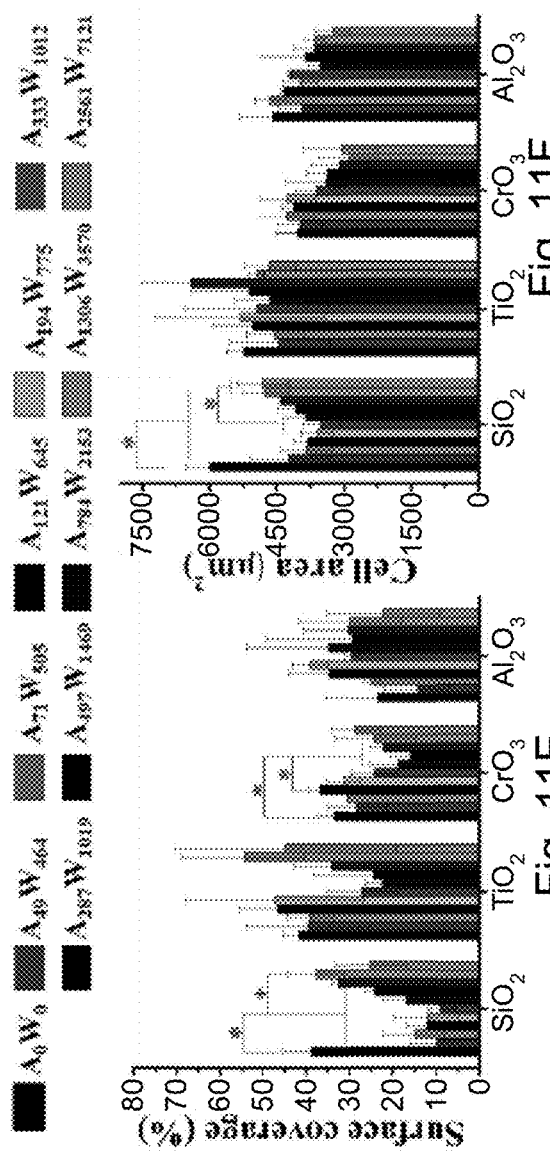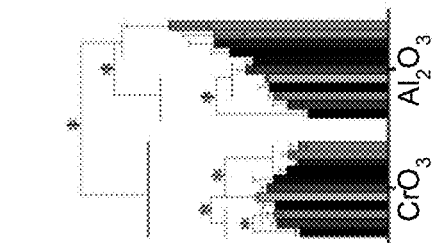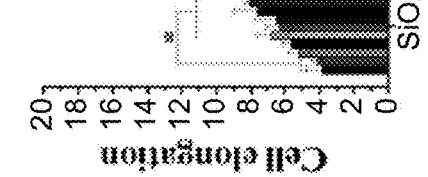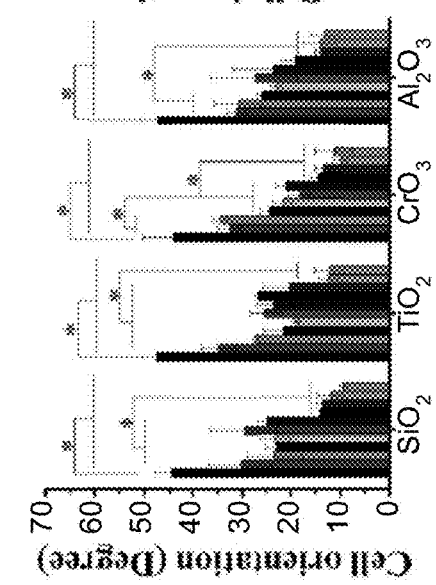

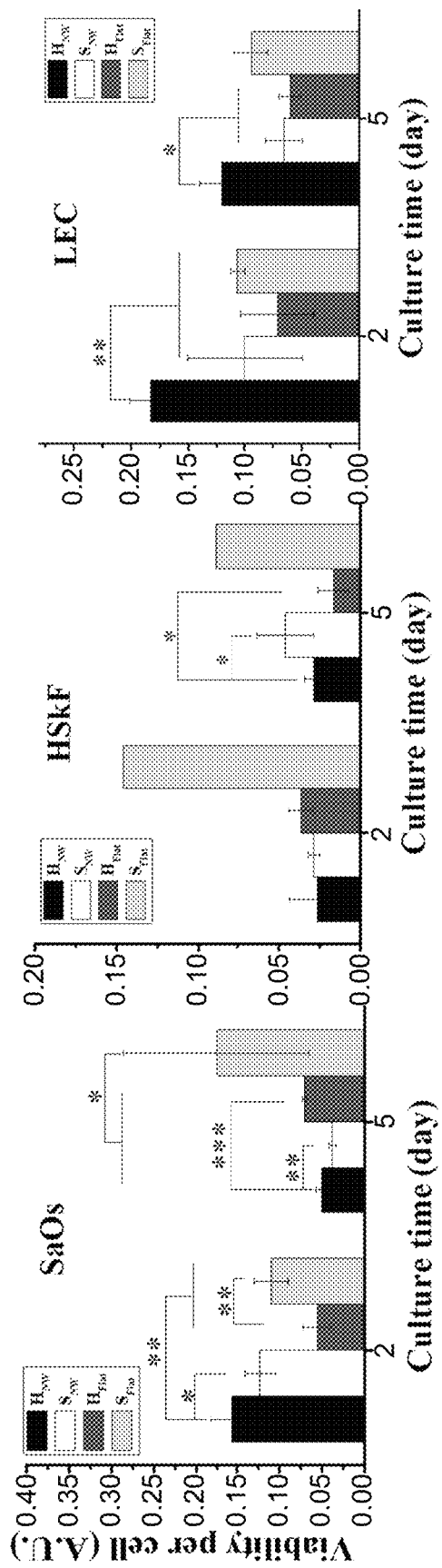
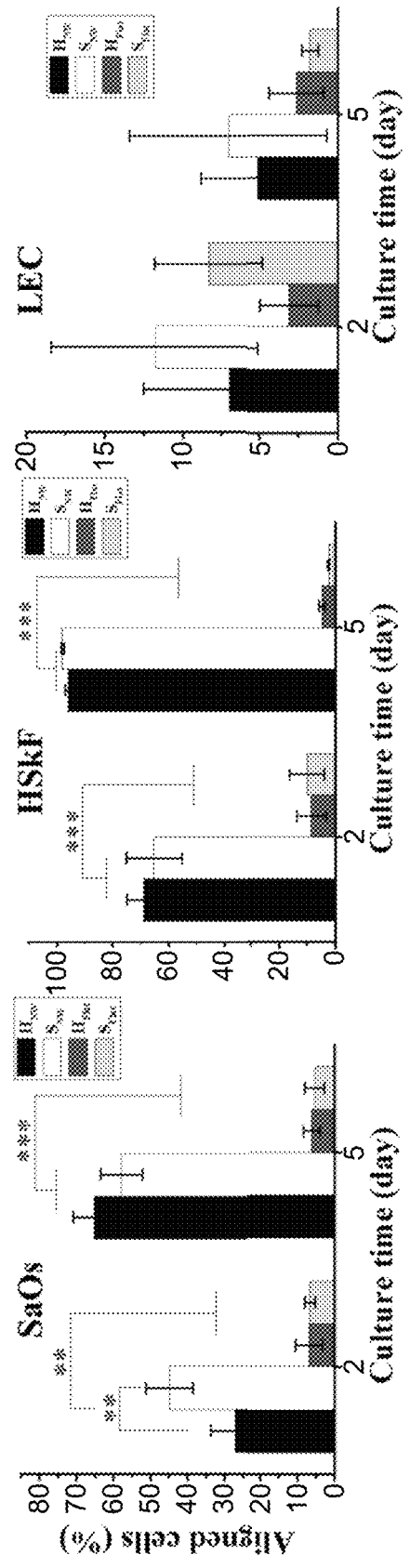
Fig. 12B  Fig. 12C  Fig. 12D
Fig. 12E  Fig. 12F  Fig. 12G

BIOMATERIAL SUBSTRATES, CELL CULTURE SYSTEMS COMPRISING THE SAME AND USES THEREOF IN CELL SCREENING APPLICATIONS

CROSS-REFERENCE TO RELATED APPLICATIONS

This application is a 371 of PCT/NL2018/050118, filed Feb. 23, 2018, which claims the benefit of European Patent Application No. 17157897.4, filed Feb. 24, 2017.

Field of the Invention

The invention relates to the fields of biomaterials, tissue engineering and regenerative medicine. More specifically, it relates to biomaterial substrates having precise surface properties and the use thereof to investigate cell-material interactions and cellular response.

Background of the Invention

For every medical implant, of which millions are used yearly ($200 billion/year, U.S.A.), secondary medical complication may arise such as but not limited to scar tissue formation (fibrosis). To minimize secondary medical complications such as fibrosis and other forms of damaged or dysfunctional tissue as well as enhancing implant efficacy and increase performance of tissue engineering scaffolds, cells need to be (re)educated to restore tissue function. Directing cellular behavior could positively impact the aforementioned applications and medical complications but directing cells efficiently is still a major challenge. Biomaterials fulfill an important role in this challenge since implants, tissue engineering scaffolds, and other medical devices come into contact with cells and tissues. When biomaterials are able to positively alter cellular behavior, fibrosis and other medical complications can be significantly reduced.

Cells are able to respond to various material surface properties such as stiffness, topology, chemistry, and wettability. They will adjust cellular adhesion properties, proliferation behavior, orientation, protein expression, and also differentiation. Knowledge about the effects of these surface confined properties onto cellular behavior will have a significant impact on the design and development of medical implants as well as scaffold materials for regenerative medicine and tissue engineering.

Tissue engineering, but in fact also medical implants, can be generally summed up as a trinity of biomaterials, cells and growth factors, combined together, with the formers playing a decisive role [1] in the generation of fully functional/healthy biological tissue. Biomaterials are nowadays seen more as a dynamic entity rather then simply passive tissue-integrating prosthetics, with the point being to create an interactive and instructive extracellular environment [2] by, e.g., mimicking the extracellular matrix as frequently attempted with hydrogels [3]. In order for cells to adequately sense and respond to a certain biomaterial, it is necessary to know what happens at the biointerface (cell-biomaterial interface). With the rise of nanotechnology tools it has been possible to take studies to a nano-scale and peer into the biophysicochemical events that take place at such a specific level [4].

Biomaterial wise, the surface is determinant in the way events take place. Once inserted into a biological environment, proteins adsorb or not to the biomaterials' surface promoting or not the adhesion of cells as embodied by the long-known process of adhesion mediated by integrins and RGD motifs [5]. In order for a cell to properly adhere to a surface, the proper proteins must adsorb to it in the first place and this adsorption is highly dependent on the surface chemistry, property that is amongst others conveyed by surface wettability [6][7].

In spite of being important, surface chemistry alone is only part of a bigger picture. Physical properties like stiffness are also pivotal in instructing cells through the risingly important effect of mechanotransduction [8][9] by which cells can translate what they feel mechanically into events as complex as the osteogenic differentiation of human mesenchymal stem cells [10]. Furthermore, the shape of the surface itself at the micro and nano levels is just as relevant as any other biomaterial surface property. Surface engineering techniques such as photolithography patterning have shown to be very important for the process of contact guidance [11] and ultimately affect processes such as adhesion and proliferation [12] [13].

Even though these surface properties play extremely important roles at the biointerface between materials and the biological environment, studying their effect on different cell types on different ranges by a single-parameter experiment approach can be extremely time consuming, if possible at all. Currently, new biomaterials are typically tested by trial-and-error, which makes the route to the clinic very costly and uncertain. This has seriously hampered the clinical translation of biomaterials. As a consequence, high-throughput platforms are avidly needed [14].

SUMMARY OF THE INVENTION

The present inventors therefore set out to develop a novel biomaterial approach that allow for the pre-screening of combined surface parameters, thereby greatly facilitating the clinical translation of biomaterials. In particular, they aimed at providing a novel platform that can be coupled to high throughput analysis capabilities and offering the possibility to integrate it into established commercial systems, thus making the technology broadly accessible and applicable.

It was surprisingly found that at least some of these goals can be met by the provision of a surface gradient approach, wherein single gradients of selected physical properties (wettability, stiffness and topography) are combined in a double orthogonal fashion. Biomaterial substrates were developed and completely characterized. Proof of concept was provided comparing the linear, double linear and double orthogonal gradients of stiffness and wettability with human bone-marrow derived mesenchymal stem cells. The surfaces were integrated into commercially available cell culture plates, making the substrates compatible with all standard analysis equipment e.g. those typically used in cell biology facilities.

Herewith, the invention provides a novel and innovative high-throughput screening platform for cell studies and the search for the ideal combination and synergistic effects of surface chemistry, mechanics and patterns by simultaneous exposing different cell types to a range of conditions and analyzing each spot on a surface where specific and different sets of conditions are encoded and gradually vary in magnitude and composition in all directions along the surface.

Accordingly, in one embodiment the invention relates to a cell culture system comprising a biomaterial substrate comprising at least a first linear surface gradient oriented orthogonally to a second linear surface gradient (i.e. two linear gradients oriented under a 90° angle), wherein said first gradient and said second gradient are selected from the group consisting of stiffness (S), aligned topography (T) and wettability (W).

Also provided is a cell culture system comprising a biomaterial substrate comprising at least a first linear surface gradient oriented orthogonally to a second linear surface gradient, wherein said first gradient and said second gradient are distinct and are selected from the group consisting of stiffness (S), topography (T) and wettability (W), provided that the system comprises at least an S gradient.

In one embodiment of the invention, said S gradient comprises a Young's modulus of 1 kPa to about 110 MPa, preferably 4 kPa to 100 MPa, for example about 1 to about 1000 kPa or 1 MPa to about 100 MPa.

In one embodiment, said T gradient comprises surface features of about 0-20 μm, preferably about 0-15 μm.

In one embodiment, the W gradient comprises a water contact angle of 20 to 110°. For example, the wettability gradient can be of various different chemical origins and may include non-charged and charged features, be it of negative or positive charge.

According to the invention, the biomaterial contains a 2 parameter orthogonal gradient wherein the parameters are selected from stiffness (S), aligned topography, or topography of other nature, (T) and wettability (W). Preferably, it contains at least a stiffness gradient.

In one embodiment, the invention provides a cell culture system comprising a biomaterial substrate comprising a S gradient oriented orthogonally to a W gradient (Ortho-Grad S/W).

In another embodiment, the invention provides a cell culture system comprising a biomaterial substrate comprising a T gradient oriented orthogonally to a W gradient (Ortho-Grad T/W).

In yet another embodiment, the invention provides a cell culture system comprising a biomaterial substrate comprising a T gradient oriented orthogonally to a S gradient (Ortho-Grad T/S).

In a still further embodiment, the invention provides a cell culture system comprising a biomaterial substrate comprising a T gradient oriented orthogonally to a double linear WS gradient (Ortho-Grad T/WS) Alternatively, the invention provides a cell culture system comprising a biomaterial substrate comprising a T gradient oriented orthogonally to a T gradient having height and pitch alter both in one direction and height altering with respect to the wavelength feature of the first (T/T).

A cell culture system of the invention may comprise any suitable biomaterial substrate or combination of substrates allowing for cell survival. In one aspect, the biomaterial substrate is a polymer, a metal or a ceramic material. The polymer may be a biodegradable polymer.

Preferred polymers include FDA-approved polymers, preferably selected from the group consisting of silicone rubber (PDMS), PLA, PGA, PGLA, PCL, PTMC, acrylate-based polymers including PMMA, PNIPAAm, PAA, PHEMA, Polyethyleneglycol (PEG)-based acrylates and derivatives thereof.

In a specific embodiment, the invention provides a cell culture system comprising PDMS comprising at least a first linear surface gradient oriented orthogonally to a second linear surface gradient, wherein said first gradient and said second gradient are selected from the group consisting of stiffness (S), (aligned) topography (T) and wettability (W). In another specific embodiment, the invention provides a cell culture system comprising PDMS comprising at least a first linear surface gradient oriented orthogonally to a second linear surface gradient wherein said first gradient and said second gradient are selected from the group consisting of stiffness (S), topography (T) and wettability (W), provided that the system comprises at least an S gradient.

Silicone rubber (PDMS) is non-toxic, transparent, flexible, biocompatible, cheap, easy to prepare, does not swell in aqueous media and is an FDA approved biomaterial. Air-plasma treatment of PDMS results in a change in stiffness which can be as low as 4 kPa when untreated and up to 100 MPa when fully oxidized.[13] This stiffness range relates well to naturally tissues (fat: ~0.1 kPa, skeletal muscle: ~20 kPa, bone: >>1 GPa).

As is exemplified herein below for PDMS, three basic approaches, involving shielded plasma oxidation are used a one sided open mask on top of the substrate providing difference in oxidation intensity as less ionized gas reaches the surface, yielding linear gradients (FIG. 1). A linear stiffness gradient is suitably formed using method "A" changing stiffness due to "long-term (300 seconds)" exposure (~top 35 nm modified). A linear wettability gradient is suitably formed using method "B" where very short treatment only affects the top molecular layer without affecting the stiffness. A linear topography gradient may be formed using method "C" where stretching PDMS before oxidation provides surface features between 0 and 14.000 nm, depending on plasma intensity and air pressure.

Typically, wettability gradients, unlike stiffness and topography, are not stable long term due to hydrophobic recovery. However, when placed in water, the gradients remain unaltered for longer periods (minimum two weeks). The orthogonal double gradients of the invention are conveniently formed by sequential combinations of methods A-C (FIG. 1) with the addition of; 1) before applying the second gradient Linear-Grad-stiffness and Linear-Grad-topography are hydrophobized with dichlorodimethylsilane as plasma activation renders it hydrophilic. Dichlorodimethylsilane reinstates nearly the same chemical surface as the starting PDMS; 2) for preparing Ortho-Grad-stiffness/topography, an imprint of Linear-Grad-topography in low modulus PDMS will be used. The imprint, by pouring liquid PDMS onto the Linear-Grad-topography with subsequent curing, provides the same topography of low modulus as the inverse of the parental wave-pattern is the same. Accordingly, in one embodiment the invention provides a cell culture system comprising PDMS comprising at least a first linear surface gradient oriented orthogonally to a second linear surface gradient, wherein said first gradient and said second gradient selected from the group consisting of stiffness (S), topography (T) and wettability (W) are obtained using shielded plasma oxidation.

The four Ortho-Grads (stiffness/topography, stiffness/wettability, topography/wettability, and topography/wettability-stiffness) are advantageously obtained by forming the second linear gradient on the first one under a 90° angle. As mentioned above, the linear S and linear T gradients need an in between modification step to obtain the Ortho-Grad-S/W and the Ortho-Grad-T/W. The Ortho-Grad-tT/S is preferably obtained using the low modulus imprint with a final treatment of hydrophobization to reach homogenous wettability. When the last step for this Ortho-Grad is omitted, the Ortho-Grad-topography/wettability-stiffness is obtained, basically our developed double linear gradient [13] orthogonally on top of the topography gradient.

The Linear-Grad-topography was also translated to FDA approved biodegradable polymers, preferably selected from PLA, PGA and PGLA, via imprinting as not to be limited to silicone rubber. By replicating the topography gradient in epoxy-resin, a hard stamp is produced for imprinting into a film of the respective biodegradable polymer. The polymer film is heated to slightly above the glass transition temperature enabling imprinting using low forces.

In one embodiment, the polymer is selected from the group consisting of silicone rubber (PDMS), PLA, PGA, PGLA, PCL and PTMC. These allow for the manufacture of a "single material only" cell culture system, wherein the gradients are formed from the original substrate material itself, e.g. using shielded plasma oxidation. This is distinct from conventional approaches using plasma polymer deposition technology described for example in Yang et al. (2009, Advanced Materials. 21(3), 300-304) wherein the substrate material is chemically modified by a plasma-polymer-deposited layer.

Other preferred biomaterial substrates are metals, preferably selected from the group consisting of Ti, $TiO_2$, $Cr/CrO_3$, $Al/Al_2O_3$, Au and Ni, and combinations thereof.

In yet another aspect, the said biomaterial substrate is a ceramic material.

In addition to the 2 parameter orthogonal surface gradients, the biomaterial may further comprise at least one additional surface gradient. For example, the further gradient may be a chemical gradient, porosity gradient, pore-size gradient, biological gradient or a viscoelastic gradient.

Prior to the invention, new biomaterials needed to be tested by trial-and-error, thus making the route to the clinic costly and uncertain. This has seriously hampered clinical translation. Pre-screening of combined physical surface parameters would greatly facilitate the clinical translation of biomaterials.

In one embodiment, the invention provides a cell screening platform comprising a plurality of distinct cell culture systems according to the invention. Preferably, all cell culture systems within the platform are made from the same biomaterial substrate and differ in their orthogonal surface gradients. For example, the cell screening platform comprises a combination of at least two, preferably at least three, more preferably four distinct 2 parameter orthogonal surface gradients selected from the group consisting of Ortho-Grad S/W, Ortho-Grad T/W, Ortho-Grad T/S and Ortho-Grad T/WS. In one embodiment, the screening platform comprises Ortho-Grad S/W, Ortho-Grad T/S and Ortho-Grad T/WS cell culture systems, more preferably all cell culture systems being based on PDMS.

In a preferred aspect, the invention provides a cell screening platform comprising at least 4 cell culture systems herein disclosed and referred to as Ortho-Grad S/W, Ortho-Grad T/W, Ortho-Grad T/S and Ortho-Grad T/WS. In such a platform, also referred to as "BiomACS", the combined effects of stiffness, topography, and wettability on cell behavior are optimized. The substrates will provide optimum parameter combinations which are translatable to implant surfaces and tissue scaffolds. BiomACS is readily integrated into commercial multiwell plates enabling its use by clinical, applied, and basic scientists.

Accordingly, the invention also provides a method for studying cellular function, comprising the steps of (a) providing a cell culture system or a cell screening platform according to the invention; (b) seeding viable cells on at least part of the surface the polymer substrate; and (c) determining the correlation of at least one cellular/biological parameter with at least two, preferably three, biomaterial properties selected from stiffness (S), (aligned) topography (T) and wettability (W).

The cells can be mammalian cells, preferably human cells, more preferably the cells selected from the group consisting of skin fibroblasts, macrophages, epithelial cells, stem cells and muscle cells.

The cells may also be bacterial cells, preferably selected from *E. coli, S. aureus, P. aeruginosa, Bacillus, Lactobacillus* or yeast cells or plant cells.

Seeding two or more different cells to obtain co-cultures are also encompassed. For example, co-cultures of mammalian cells and bacterial cells can be grown on the polymer substrate.

The step of determining the correlation of at least one cellular/biological parameter with at least two biomaterial properties may comprise determining adhesion, morphology (such as shape, spreading and/or orientation), migration, proliferation, contact, differentiation, survival, protein expression, gene expression, and any combination thereof may be assessed.

A biomaterial of the inventions is unique in that it can, chemically and physically, supports and organizes tissue architecture. It can provide many specific combinations of physical surface parameters, allowing for example for efficient cell-material interaction studies.

Cell function studies may include determining proliferation, apoptosis, cytoskeleton, adhesion properties. It may also include measuring the production of "intervention responsive" genes and gene products or physiological responses such a specific growth factors, cytokines, chemokines, reactive oxygen species. Biological responses are suitable detected by specific genetic reporter constructs known in the art, such as EGFP, dTOMATO, or Luciferase genes coupled to the promotor region of responsive genes. Measurements may be done using specific layers of cells, including mesenchymal stem cells, endothelial cells, epithelial cells, smooth muscle cells, fibroblasts and their derived cell lines. Physical interactions between material and cells or cell-monolayers and cell multi-layers may be determined. In one embodiment, one or more biological responses are recorded in real time.

Whereas the advanced cell-material screening platform development as exemplified herein below in the Examples is based on silicone, it is suitably translated to different biomaterials, including metals/Metal oxides, Ceramics, $Ti/TiO_2$; $Al_2O_3$; $SiO_2$; Au; $Cr/CrO_3$; hydrogels of diverse composition including molecular hydrogels, polymeric hydrogels and hydrogels of natural origin; molecular monolayers of diverse composition both synthetic and natural origin.

A cell screening platform provided herein can facilitate a multitude of applications including various biomedical applications. For example, material properties for minimizing silicone implant induced fibrosis can be identified. As another example, skeletal muscle tissue engineering scaffolds or a multiwell muscle-plate for patient-specific metabolic disease diagnosis can be developed.

The invention also relates to the use of a cell culture system, a cell screening platform and/or a method according to the invention in tissue engineering, drug discovery, medical device benchmarking, implant technology, or specialized cell culturing. Advantageously, a drug screening platform for developed tissues based on scaffold design originating from screening findings using a plurality of distinct 2 parameter orthogonal surface gradients, e.g. BiomACS, is provided. The invention also finds it use for tissue mimicking platform substrates e.g. for benchmarking medical devices such as catheters.

BRIEF DESCRIPTION OF THE DRAWINGS

FIG. 3—Topography, Wettability and Stiffness Triple Gradient. A) Linear representation of the Stiffness Gradient along the y-axis (coaxial with wettability). B) Linear representation of the wettability gradient along the y-axis. C) Linear representation of the imprint topography features gradient along the x-axis. D) Planar representation of the wettability and stiffness gradients on the topography gradient. Stiffness (MPa) is represented by gray scale sections and wettability (WcA) by black line density sections.

FIG. 10—Overview scheme of differentiation process of satellite cells to myofibers (A) and topography sample preparation (B) Cell alignment and myotube formation in nanowrinkled surface after Gd in differentiation medium as compared to TCP displays the enormous difference in morphology where the surface topography induces a more natural skeletal muscle orientation (C).

The invention is illustrated by the following non-limiting examples.

EXPERIMENTAL SECTION

Materials and Methods
PDMS Preparation

Polydimethylsiloxane (PDMS) surfaces were prepared from a commercial elastomer kit (Dow Corning). The prepolymer and crosslinker were mixed at a 10:1 ratio. From this mixture, 30 g were poured on 12×12 cm petri dishes ensuring an equal thickness between samples. The mixture was then placed in a vacuum oven at approximately 200 mtorr for gas removal until no air bubbles were present in the samples. The PDMS was then cured at 70° C. overnight to ensure complete crosslinking.

Figure 1:
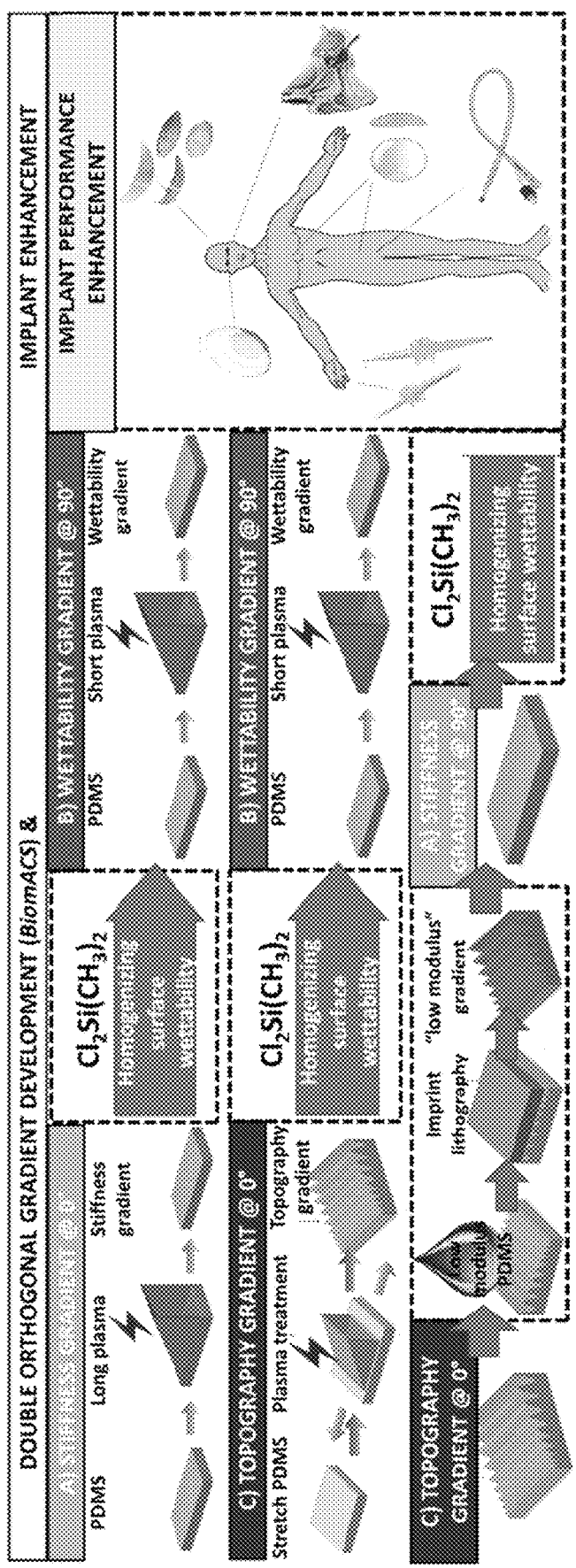
FIG. 1—Overview for engineering the orthogonal gradients of the invention (BiomACS platforms). These are translated towards tissue engineering e.g. minimization of silicone implant associated fibrosis, muscle engineering for facial palsy and a 96-muscle on a plate as a patient-specific diagnosis tool for Multiple acyl-CoA dehydrogenase deficiency (MADD).

A) Generation of Orthogonal Topography and Stiffness-Wettability Double (T/S-W) Gradient A.1 Generation of Topography (T) Gradient In order to obtain a topography gradient, PDMS surfaces were stretched by 30% using a specially built device, as seen in FIG. 1. After this stretching, a metal mask with a 30° angle and 2.6 cm of length (resulting in 2 cm after removing the stretching) was placed on top of the surface and it was then exposed to air plasma generated in a plasma oven (Diener Electronic—Atto Model). The plasma pressure was adjusted in order to be stable at 25 mtorr and the electrodes were turned on for 650 s, 100% plasma intensity. After the plasma treatment, the stretching was released and the sample taken from the stretcher. To ensure a uniform surface stiffness and topography stability, all the topography gradients were post treated for 10 minutes in plasma at 200 mtorr.

For the Fibrotic response tests, smaller 1 cm gradients were produced in the same manner. The small ranging gradients were exposed to 60 mtorr plasma for 100 s while the large ranging ones were exposed to the same conditions as the 2 cm gradients described above.

A.2 Topography Gradient Imprinting

Due to plasma oxidation, topography gradients have an increased stiffness in comparison to non-oxidized PDMS. In order to obtain the topography gradient without increased stiffness it was necessary to imprint the gradient features into fresh PDMS. In order to do so, gradients that were used for imprinting were treated with an additional 120 mtorr oxidation for 10 minutes and stored for at least 3 days, in order to make sure there was no excessive reactivity that could compromise the imprinting process. After this, fresh PDMS was poured on top of the gradients and degassed in the vacuum oven. The imprinting took place at 70° C. overnight, curating the fresh PDMS allowing it to be peeled off and separated from the original gradient after complete crosslinking.

A.3 Generation of Orthogonal Stiffness/Wettability and Topography Double (SW/T) Gradient The triple gradient of Stiffness/Wettability and topography was generated by modifying a topography imprint with plasma oxidation for 1 minute at 30 mtorr using a 2 cm 30 mask perpendicular to the topography gradient direction.

B) Generation of Orthogonal Stiffness and Topography Double (S/T) Gradient

In order to generate a stiffness and topography double gradient it was first necessary to create a triple gradient as described in (A.1-3) After this, the triple gradient was submitted to a liquid-phase modification in a solution of 30 mL Ethanol Absolute+2.4 mL Ammonia Hydroxide (30%)+ 80 µL Trimethoxypropylsilane. The samples were then rinsed in absolute ethanol to remove any remaining contaminants. This modification created a hydrophobic monolayer thereby removing the wettability gradient.

C) Generation of Orthogonal Wettability and Topography Double (W/T) Gradient

In resemblance to the linear wettability gradient generation, topography imprints (A.2) were oxidized in plasma for 1 minute at 200 mtorr. This resulted in a uniformly soft yet slightly-stiffer-than-unmodified surface due to the fact that oxidation times over 1 minute would result in the loss of topography height and so this time was used to keep a similar topography between all gradients. After this, the oxidized imprints were modified in liquid as described in (B). After drying, a wettability gradient was generated by modifying the hydrophobic monolayer using a 2 cm-30° mask perpendicular to the topography gradient and placing the sample in 500 mtorr plasma for 20 seconds. This resulted in a wettability gradient orthogonal to the topography, with a uniform stiffness.

D) Generation of Orthogonal Wettability and Stiffness Double (W/S) Gradient

D.1 Generation of Linear Wettability and Stiffness Gradients

Figures 2A, 2B:
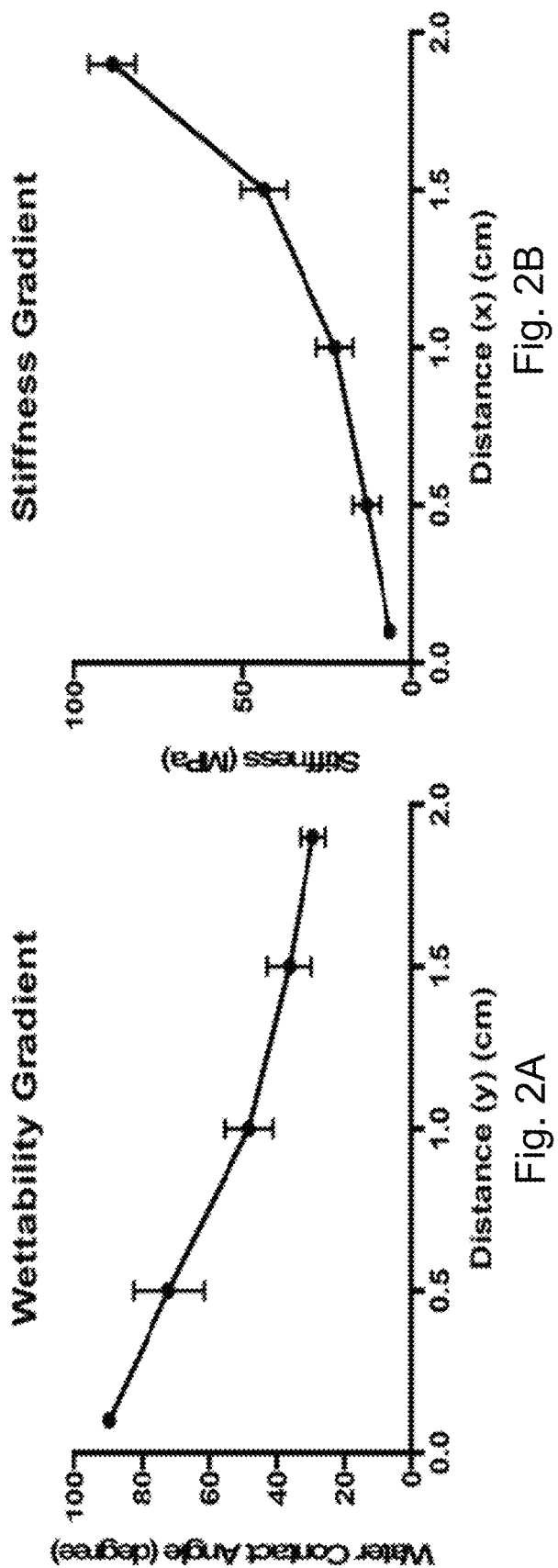
FIG. 2—Double Orthogonal Stiffness and Wettability Gradient. A) Linear representation of the wettability gradient that exists along the y-axis. B) Linear representation of the Stiffness Gradient that exists along the x-axis. C) Planar representation of the orthogonal double gradient. Stiffness (MPa) is represented by gray scale sections and wettability (WcA) by black line density sections.

The generation of wettability and stiffness gradients was achieved by exposing the PDMS surface to plasma for 1 minute at 30 mtorr with a 2 cm-30° mask covering the gradient area and no stretching. As illustrated in FIG. 2, plasma oxidation causes the PDMS surface to become stiffer and more wettable, increasing both parameters (wettability and stiffness) as the surface approaches the mask opening. This results in a double linear (both vary in the same direction) gradient of wettability and stiffness.

D.2 Generation of Stiffness (S) Gradients

In order to isolate the stiffness gradient from the obtained from (D.1) the double linear gradient was modified overnight in a liquid solution of 30 mL Ethanol Absolute+2.4 mL Ammonia Hydroxide (30%)+80 µL Trimethoxypropylsilane. The samples were then rinsed in absolute ethanol to remove any remaining contaminants. This modification results in a hydrophobic monolayer thereby removing the wettability gradient while keeping the stiffness one.

D.3 Generation of Wettability (W) Gradients

To generate a single wettability gradient, unmodified PDMS surfaces were oxidized in plasma for 10 minutes at 200 mtorr, generating a stiff and active surface which then was liquid modified as described in (D.3). After drying from the ethanol rinsing, a wettability gradient was created by using a 2 cm-30° mask and placing the sample in 500 mtorr plasma for 20 seconds. This short and high-pressure oxidation allows for monolayer modification and wettability gradient generation without altering the stiffness of the PDMS beneath.

D.4 Generation of Orthogonal Wettability and Stiffness Double (W/S) Gradient

Double orthogonal wettability and stiffness gradients were obtained by using linear stiffness gradients as resulting from (D.2) and then placing a 2 cm-30° mask with a 90 orientation in relation to the stiffness gradient and placing the sample in the plasma oven for 20 seconds with a pressure of 500 mtorr (similarly to D.3). By doing so, a wettability gradient orthogonal to the stiffness gradient was generated by modifying the monolayer alone therefore not affecting the stiffness gradient.

2.2. Gradients Characterization

Gradients were characterized in concern to their stiffness, wettability and topography, depending on which kind of gradient was present on the sample.

2.2.1. Topography and Stiffness Characterization

Topography characterization was done using an Atomic Force Microscope (Veeco Dimension V, Dimension™ V 3100 Atomic Force Microscope, Bruker, USA) working in contact in air mode. Topography pictures chosen size was 20 µm² and the wrinkles were characterized by their wavelength and height.

Stiffness Characterization was measured by the surface Young's modulus using the same AFM device with nanoscope V as software for the force curve processing. In total, 25 force curves were taken per analyzed spot.

All AFM data was obtained using Bruker Cantilevers made from silicon nitride with silicon tips.

2.2.2. Wettability Characterization

The wettability of samples was measured using a custom-built tensiometer, using 2 µL droplets of mili-Q water in a sessile drop method. The water contact angle value and droplet pictures were obtained using a specifically coded Matlab program.

2.6 Cell Adhesion Studies

Human bone marrow mesenchymal stem cells (hBM-MSCs, Poietics™, p7, Lonza) were used in order to study cellular adhesion on the different wettability and stiffness surfaces. The growth medium that was used consisted of Dulbecco's MEM Alpha Medium (1×) supplemented with GlutaMAX, 10% FBS (fetal bovine serum) and 0.1% AA2P (ascorbic acid 2-phosphate). The cells were incubated at 37°, 5% $CO_2$. All PDMS 2×2 cm gradients were sterilized with 70% ethanol and dried or washed with PBS before use. Following this, hBM-MSCs were seeded onto the PDMS surfaces at a density of 3*10⁴ cells/well in 6-well plates. The cells were then placed back into the incubator at 37° and 5% $CO_2$ for 3 h and 24 h.

2.6.1 Fibrotic Response Studies

In order to assess the extent to which surface topography plays a role in the transition to and from a fibrotic phenotype, Human Skin Fibroblasts (HskF ccd11125k, p12) and Lense Epithelial Cells (LEC (B3), p19) were separately cultured on 1 cm topography gradients with small (60 mtorr 100 s) and large (25 mtorr 650 s) feature size ranges as previously described in 2.2. The growth medium that was used for the HskF cells consisted of RPMI Medium supplemented with 10% FBS and 1% Pen/Strep (antibiotics). For the LEC cells the medium was composed by Eagle's MEM Medium (EMEM) supplemented with 20% FBS, 1% Glutamax, 1% Na Pyr and 1% Pen/Strep. The cells were incubated at 37°, 5% $CO_2$. All PDMS 1×1 cm gradients were sterilized with 70% ethanol and dried before use. After the sterilization HskF and LEC cells were seeded onto the samples at a density of 1*10⁴ cells/well in 24-well plates. The cells were then incubated for 2 days at 37° C. and 5% $CO_2$.

2.6.1 Cell Analysis

To evaluate cell adhesion, the cultured hBM-MSCs were fixated with 3.7% paraformaldehyde in PBS for 20 minutes. 24 h Samples were immuno-stained with a primary antibody against vinculin (Mouse-anti-human Sigma, 1:100 concentration) in combination with a secondary FITC-labeled goat-anti-mouse antibody (1:100 concentration). In addition, DAPI and TRITC-phalloidin were used to stain cell nuclei and F-actin, respectively. For the 3 h samples the staining was done using only DAPI and Phalloidin since the short time would not enable such focal adhesion maturation. Cells were observed using TissueFaxs, with a Zeiss Axiolmager Z1 Microscope System (Tissue-Gnostics GmbH, Vienna, Austria) at 10× magnification. The whole samples were scanned and the individual pictures combined together with the Tissue-Gnostics software, that was also used to quantify cell spreading and cell adhesion by calculating the average cell area and number of cells on each analyzed spot.

To evaluate the fibrotic response to topography gradients, HskFs and LECs were fixated in the same manner. Both cell lines were stained with a primary antibody against alpha smooth muscle actin (α-SMA) (Mouse-anti-human Sigma, 1:100 concentration) in combination with a secondary FITC-labeled goat-anti-mouse antibody (1:100 concentration). Also, for both cell lines, DAPI and TRITC-phalloidin were used to stain cell nuclei and actin cytoskeleton. In addition to this, HskFs were stained with a primary antibody against collagen (rabbit-anti-human 1:500) in conjunction with a secondary donkey-anti-rabbit LRSC-labeled antibody. Cells were observed using TissueFaxs, with a Zeiss AxioImager Z1 Microscope System (Tissue-Gnostics GmbH, Vienna, Austria) at 10× magnification. The whole samples were scanned and the individual pictures combined together with the Tissue-Gnostics software. Cell Area, Orientation and Elongation were quantified using the Image-J software (FIJI).

Example 1: Orthogonal Wettability and Stiffness Double Gradient (W/S)

Separating wettability and stiffness gradients from each other offers a way to study the influence of the two different parameters independently. However, the synergistic effect of both properties can result in different cellular responses than those that arise from each gradient alone [35]. The double linear wettability and stiffness gradient can already provide an idea of how simultaneous stiff and hydrophilic or soft and hydrophobic substrates can alter cell fates but the limitation of such a gradient is the fact that both parameters vary in a double linear way, i.e., stiffness increases as wettability increases and it is not possible to see how cells respond to, e.g., a stiff but hydrophobic substrate or vice-versa. In order to solve this, a double orthogonal gradient was developed in a way that stiffness and wettability vary not linearly but orthogonally, as shown in FIG. 2. By doing so, every line with a fixed wettability comprises all the stiffness values of the gradient and the same holds true for stiffness. It is therefore possible to study every wettability value for every stiffness value, in combination. Therefore, this method generates a high amount of conditions within one single surface, where two parameters vary independently in spite of being combined together.

Figure 2C:
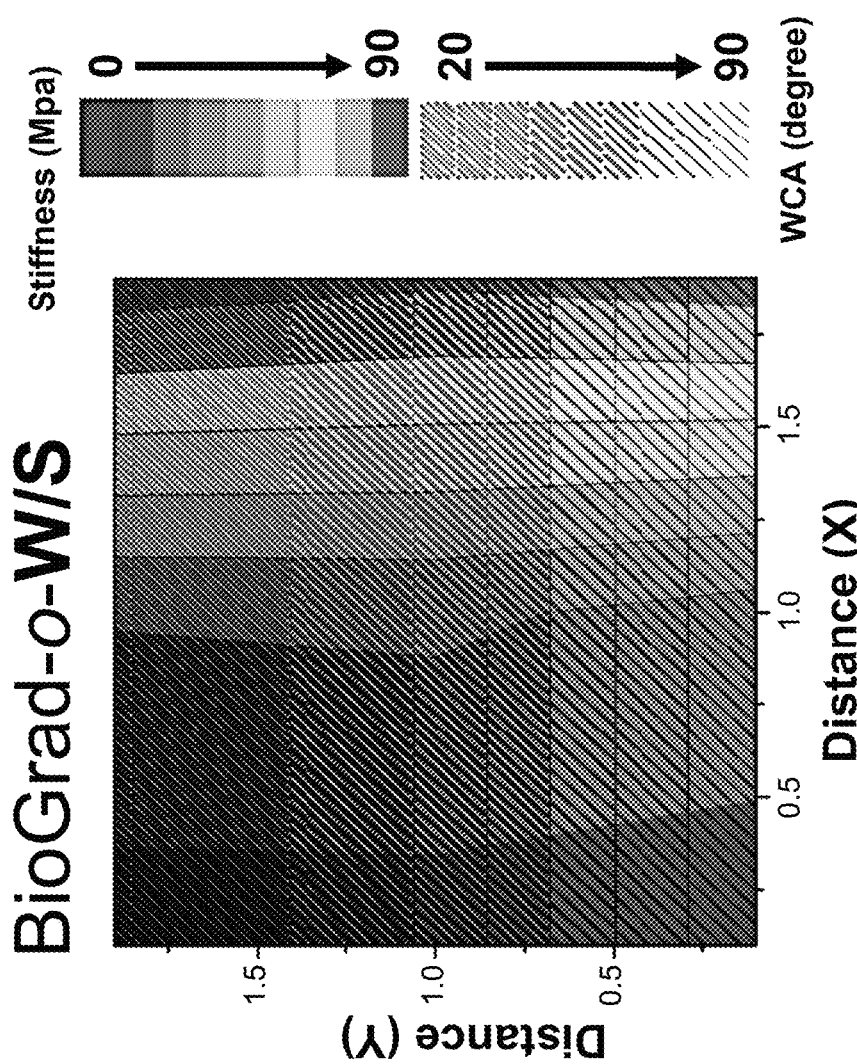

As represented above, the engineered surface has two gradients orthogonal to one another. On the x-axis, stiffness increased from 6.41 MPa to 88.82 MPa while on the y-axis the water contact angle went from 89.7° to 29.3°. As shown in FIG. 2C, it is possible to single-out any combination of wettability and stiffness comprised within both gradients therefore solving the problem of linear dependence present on the first shown double gradient.

Example 2: Orthogonal Topography and Wettability/Stiffness Gradients

Equally important to the surface chemistry and physical properties is the surface topography. As previously shown [25], this kind of PDMS topography gradients affect the way cells are guided along the surface influencing responses like adhesion, spreading and orientation. Nevertheless, just as stiffness and wettability can synergize in a way that both together result in different outcomes than the sum of parts, biomaterials' surface patterns have too shown to have a synergistic effect with physical properties as stiffness and rigidity [36] [37]. To allow high throughput investigation of this effect, wettability and stiffness gradients were combined with topography gradients.

By exposing a PDMS surface on which a topography gradient is imprinted to shielded plasma, a double linear gradient in wettability and stiffness is created on top of the wrinkled surface, as seen on FIG. 3, similarly to what happens on a planar surface. The stiffness gradient ranged from 4.62 MPa to 105.48 MPa along the 2 cm y-axis whereas the wettability went from a water contact angle of 95.3° to 27.0°.

As can be seen in FIG. 3D, stiffness increases as the features turn smaller. This effect is likely due to the different aspect ratios between wavelength and height. Since stiffness is measured by AFM tip indentation, the topography shape affects the way the tip percepts the surface. For example, if the measurement is made on the top or bottom of the wrinkles it yields a much higher and realistic stiffness value than when the measurement is made in the descending or ascending portion of the wrinkle. This is due to the fact that on the latter positions, the AFM tip senses a higher area therefore resulting in a lower indentation force (pressure/area) and, consequently, a lower stiffness value. As wrinkles become smaller, the aspect ratio changes and this results in slightly increased stiffness values but these do not necessarily mean that the real stiffness is different, only the measured value is affected.

It is also important to notice that wettability, being a macroscopic property of the surface, is influenced by topography since water droplets change their shape when they come in contact with the surface wrinkles tending to follow their shape when these are hydrophilic, extending one of the droplet's axis, and causing them to be even less spread over when the wrinkled surface is hydrophobic. However, as can be seen in FIG. 3, the wettability gradient obtained was still very much similar to those obtained on planar surfaces, even though water spreading can be altered by the existing topography.

Example 3: Orthogonal Topography and Stiffness Gradient

Figure 5:
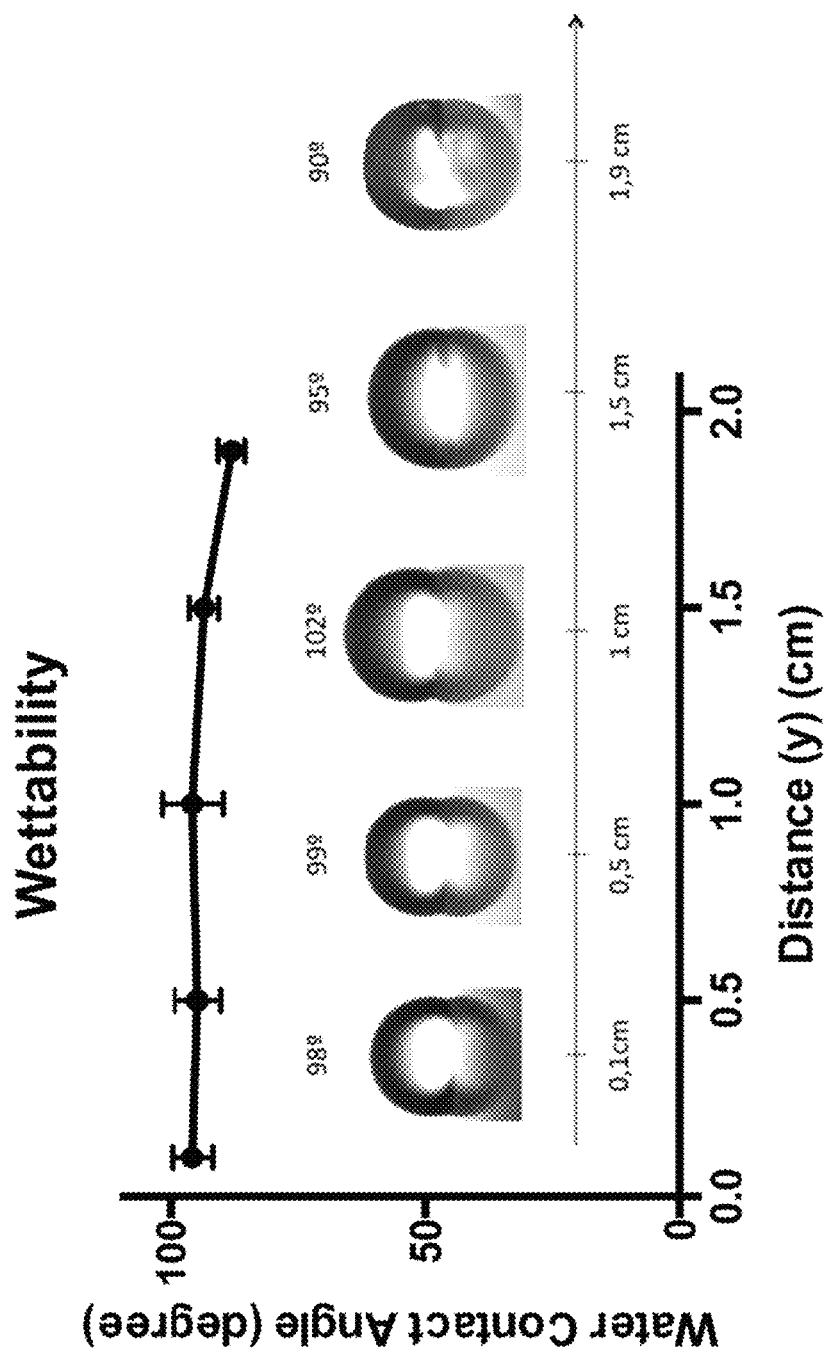
FIG. 5—Water contact angle pictures taken on the double orthogonal stiffness and topography gradient, along the original wettability gradient axis.

The triple gradient contains already several data on one single surface. Nevertheless, once again, it was necessary to decouple wettability from stiffness in order to allow the analysis of the way stiffness and wettability alone influence topographical cues. Similarly to what was done to isolate a stiffness planar gradient, the triple wettability/stiffness gradient was modified in liquid phase with a trimethoxypropylsilane hydrophobic monolayer. By doing so, the wettability gradient was no longer present, instead, all points along the y-axis possessed a water contact angle between 900 and 100°, as shown in FIG. 5.

Figures 4A, 4B:
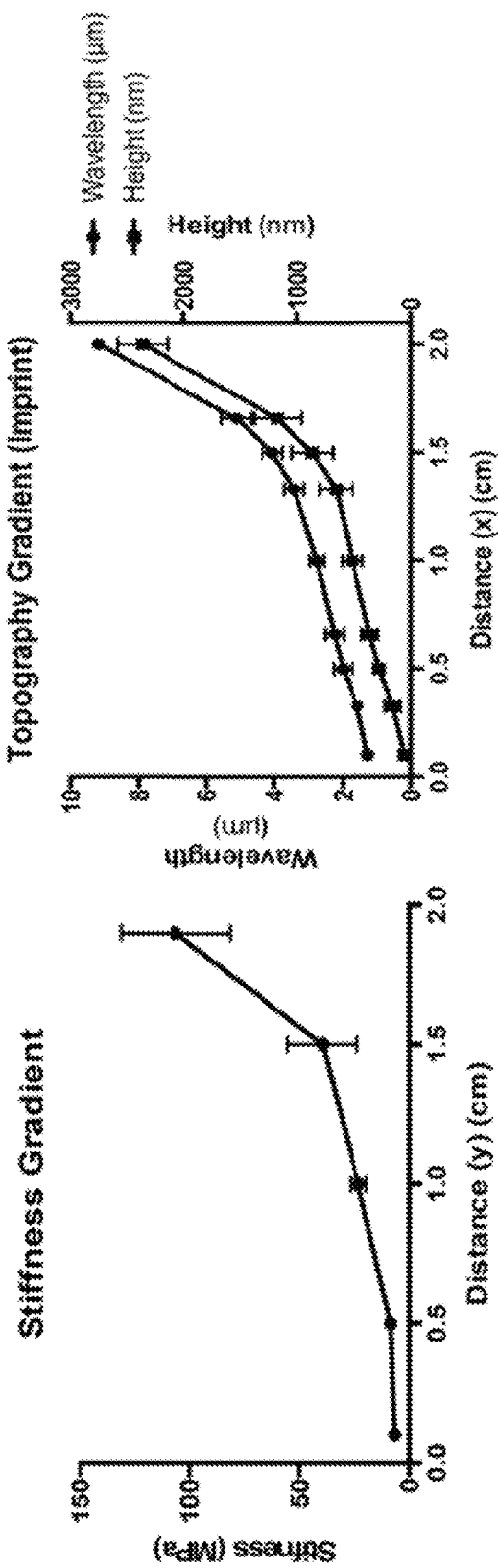
FIG. 4—Topography and Stiffness Double Orthogonal Gradient. A) Linear representation of the Stiffness Gradient along the y-axis. B) Linear representation of the imprint topography features gradient along the x-axis. C) Planar representation of the stiffness gradient orthogonal to the topography gradient. Stiffness (MPa) is represented by gray scale sections.
Figure 4C:
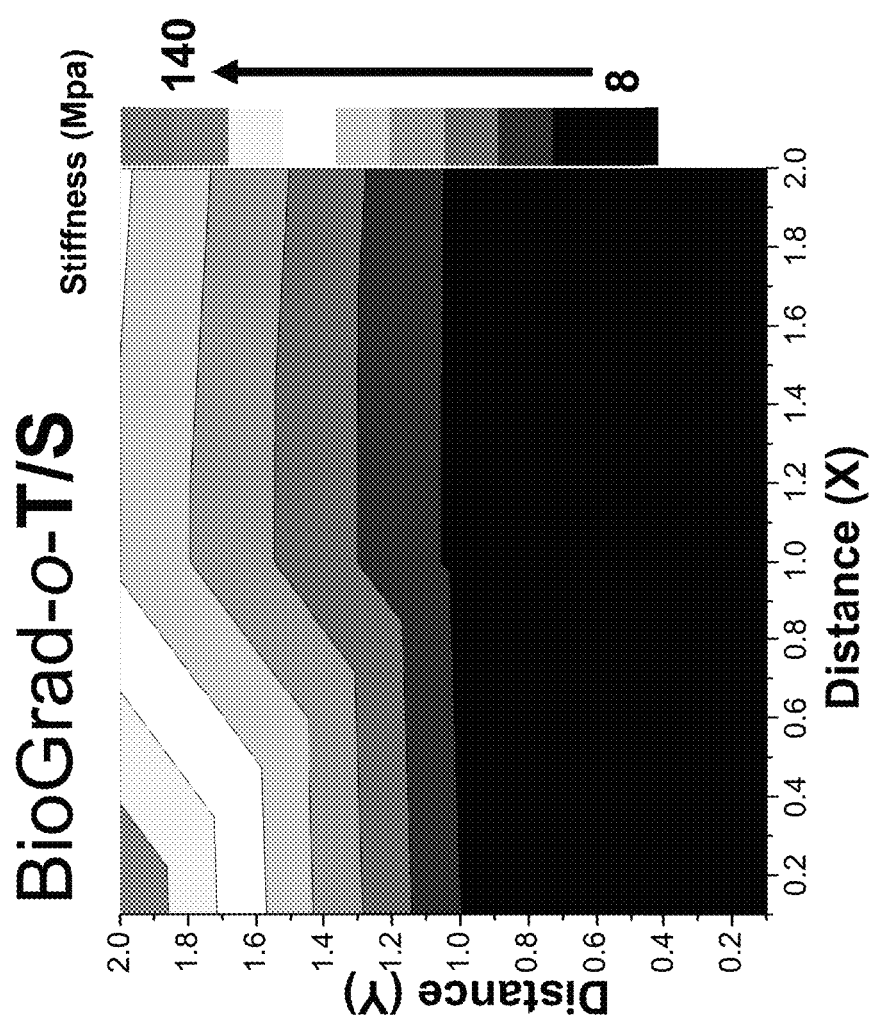

Once again the topography is the same as any other PDMS imprint here described and also shown in FIG. 4B. It is important to notice that the liquid modification was identified as responsible for the appearance of random wavy features on the surface near the edges where the plasma-shielding mask ended. This effect on the PDMS is something to study and improve in the future in order to have a completely perfect gradient even at the edges. Due to this observance, most of the characterization was done between 0.1 and 1.9 cm therefore avoiding these emerging edge effects. Apart from this minor detail, the stiffness gradient was conserved and not affected by the modification along the surface as shown in the 2D map in FIG. 4C. The gradient map is very similar to the one on the triple gradient shown in FIG. 3D, with the same stiffness variation with the aspect ratio. The overall stiffness gradient here went from 6.62 MPa at 0.1 cm to around 106.59 MPa at 1.9 cm being once again within the trending range with the difference being the uniform wettability as confirmed in FIG. 5.

Example 4: Orthogonal Topography and Wettability Gradient

For the last gradient, it was necessary to engineer a way to create a wettability and topography orthogonal gradient. The first attempt here was to repeat the procedure used for the single linear wettability gradient that involved a 10 minutes uniform and unmasked oxidation followed by a monolayer modification and high-pressure plasma gradient generation on that same monolayer. However, when repeating the process it was noticed that the imprint was more sensitive to unmasked plasma exposition with the uniform 10 minutes oxidation causing a flattening of the topography in a way that the wrinkles were present and had the same wavelength but a decreased height therefore resulting in half of the gradient being almost flat.

Figure 6A:
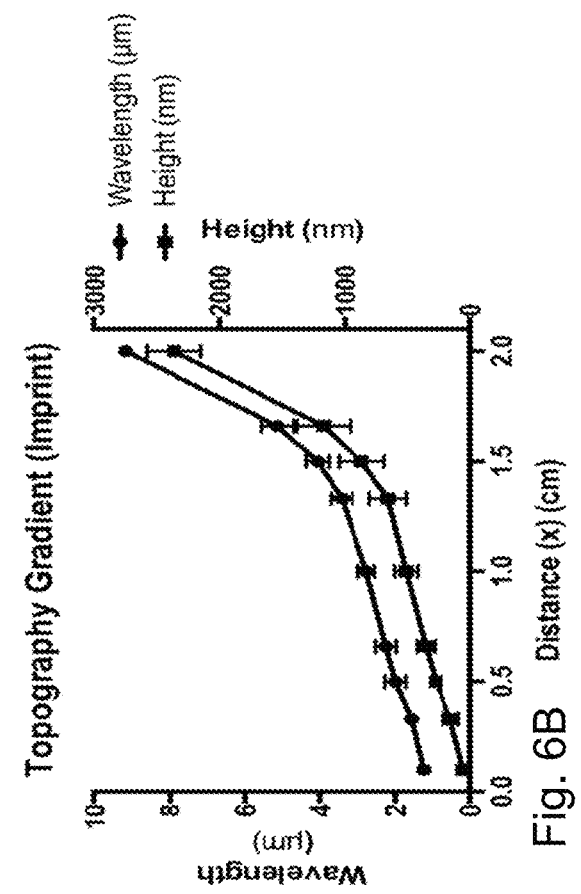
FIG. 6—Topography and Wettability Double Orthogonal Gradient. A) Linear representation of the wettability gradient along the y-axis. B) Linear representation of the Stiffness along the y-axis (coaxial with wettability). C) Linear representation of the imprint topography features gradient along the x-axis. D) Planar representation of the surface stiffness and wettability on the topography gradient. Stiffness (MPa) is represented by gray scale sections and wettability (WcA) by black line density sections.
Figure 6B:
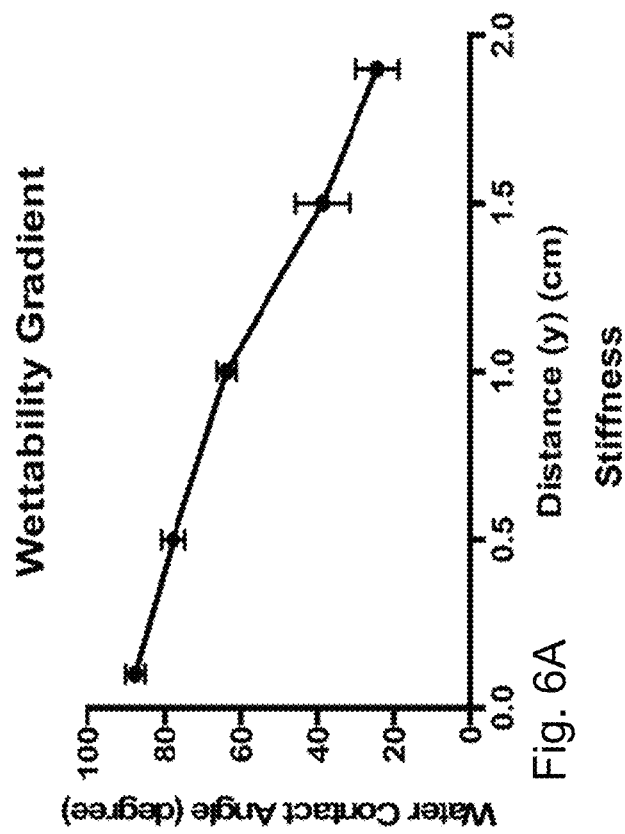
Figure 6C:
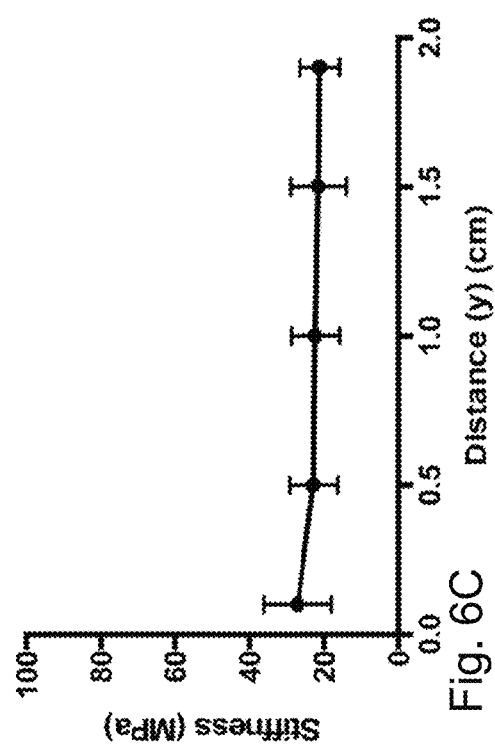
Figure 6D:
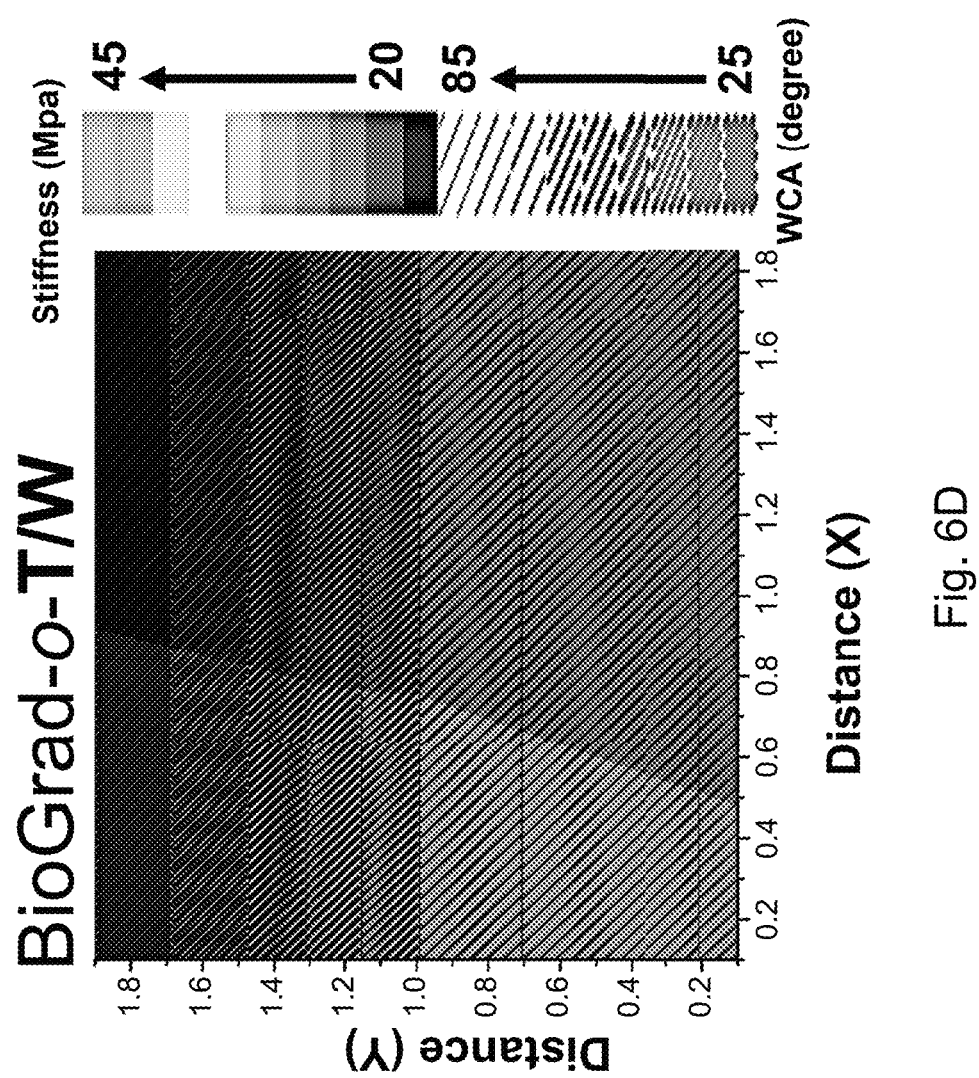

To circumvent the topography loss, the imprinted gradient was oxidized for a shorter time (1 minute) and then liquid modified to generate the trimethoxypropylsilane monolayer. Using then high-pressure short-timed plasma and a metal mask, a wettability gradient was generated on the monolayer alone, with a water contact angle ranging from an average of 87.7° to 24.3°, as represented on the graph on FIG. 6A. In this double gradient, the stiffness is lower than on the planar wettability gradient due to the shorter oxidation time. However, this is not a problem because the stiffness is uniform along the y-axis between around 27 and 21 MPa and also all over the surface as mapped in FIG. 6D. Once again, the higher registered stiffness values happen on the smaller aspect ratio side of the gradient, as clearly distinguished by the two tones of gray on the stiffness map (FIG. 6D). However, this difference is not relevant since it is around 5 MPa on 21-27 MPa magnitude. This allows the imprint topography to suffer no changes being once again the same as the original imprint (FIG. 6C), with no height reduction.

With this last gradient, every combination of wettability, topography and stiffness gradients is achieved allowing for single, double linear and double orthogonal studies of cell behavior in response to several different conditions at once.

Example 5: Cell Culturing on a W/S Orthogonal Gradient

Bone marrow MSCs were cultured for 24 h on a double orthogonal wettability and stiffness gradient as shown in FIG. 7 so as to explore all the ways through which wettability and stiffness changes can alter cell behavior.

Figure 7A:
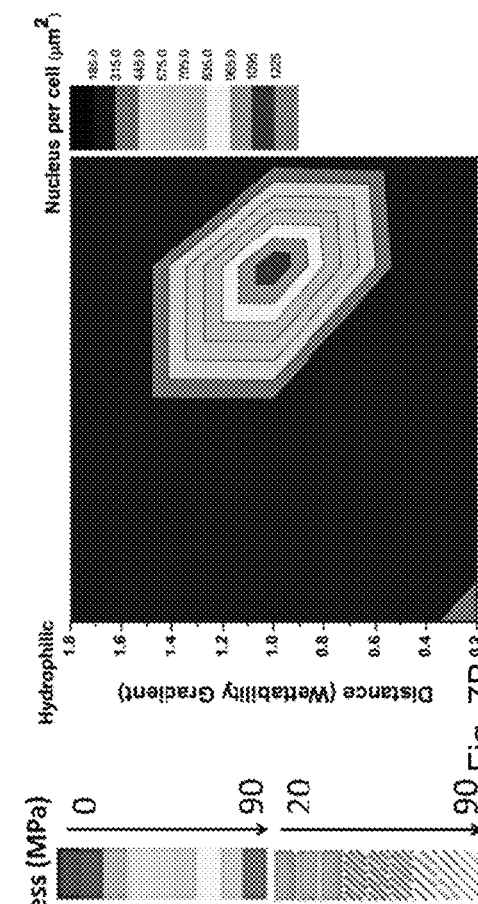
FIG. 7—hBM-MSCs cultured on a double orthogonal wettability and stiffness gradient (A). The evolution of wettability and stiffness can be seen on the corresponding axis. Analysis based on quantitative fluorescence microscopy imaging where cell staining was applied TRITC-Phalloidin (actin), DAPI (nuclei), and. vinculin staining (focal adhesions). Quantitative analysis results in 2D density plots for: B) nucleus area ($\mu m^2$/nucleus); C) cell spreading ($\mu m^2$/cell) and; D) focal adhesion area per cell ($\mu m^2$ adhesion/cell). Density plots have the respective gray scale on the right side of the plot.
Figure 7C:
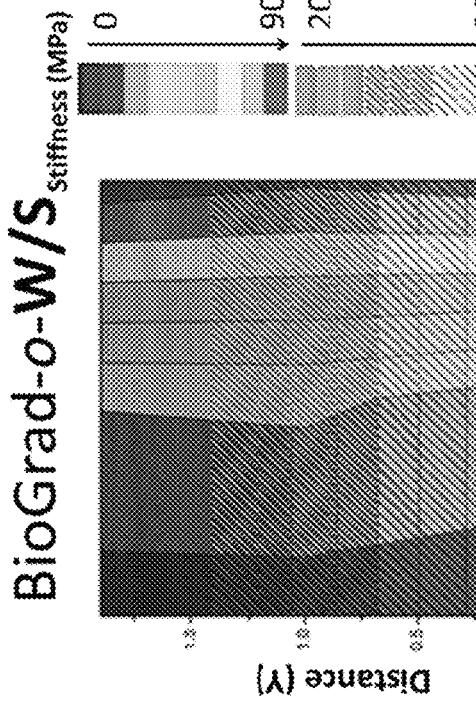
Figure 7B:
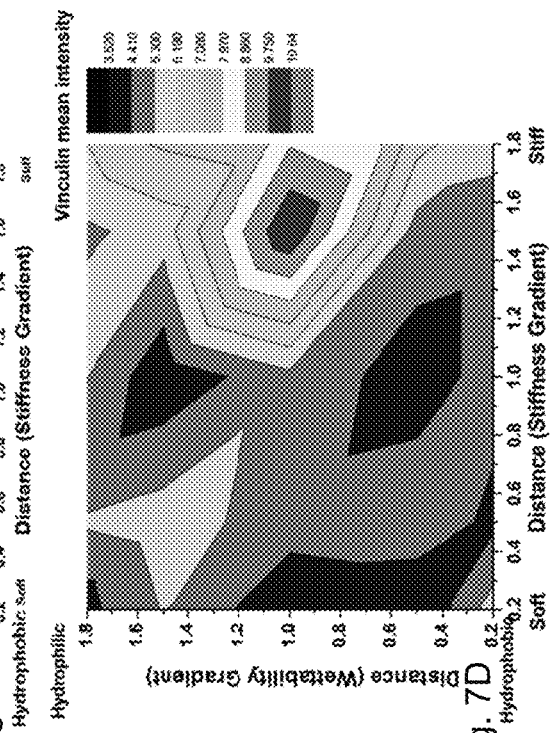
Figure 7D:
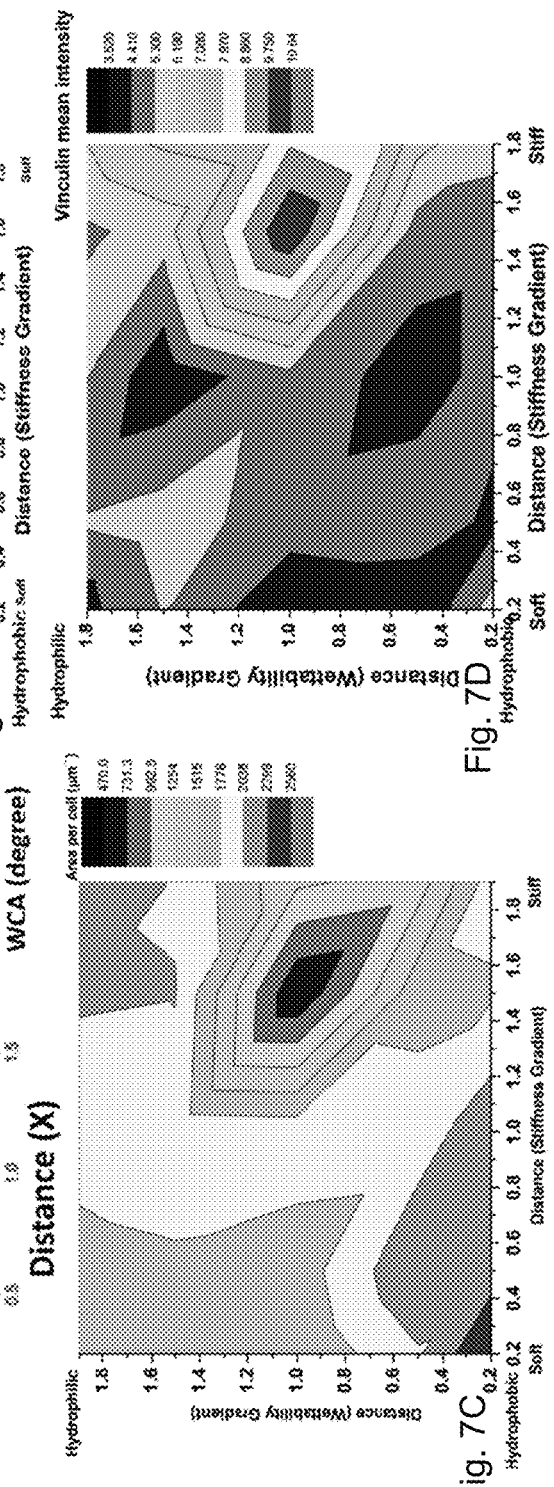

By dividing the whole gradient in 144 sections (12×12) it was possible to measure nucleus size, cell area and adhesion (focal adhesion) and plot it as an intensity map depicted in FIG. 7B-D. These maps show the power of using an orthogonal gradient. By looking at the diagonal from hydrophobic and soft to hydrophilic and stiff, it is possible to get the same information as from the double linear gradient, hydrophobic and soft has worse cell spreading when compared to hydrophilic and stiff, as seen in FIG. 7C where cell spreading and hence the cell area increases significantly, as was found on the double linear gradient. However, the double orthogonal gradient not only comprises the information that the double linear already had. It is possible to see, e.g., that hydrophilic and soft is even better for cell adhesion with the highest cell area being detected here. Also, it's possible to see a weak spot at high-stiffness and mid-wettability showing very low cell areas. Conversely, at mid stiffness and low wettability there is a spot revealing some preference for that set of conditions.

In all analysis, it is seen that there is a particular behavior which is localized at the stiff side of the substrate at intermediate wettability. When using all linear gradient described so far, none of the linear gradient properties by themselves would enable to recreate these particular combined surface properties.

Taking all this into consideration, it is clear that the creation of gradients in a double orthogonal fashion yields a very powerful platform that not only covers a lot of information from single and double linear gradients but also shines a light in specific parameters combinations that were present in no other gradient. Also, since for every value of one parameter all the values of the other are conserved, it is possible to search for the specific optimal condition for a given cell type. It is also worth noticing that even though it is possible to see some significant differences in simple cell responses as the tested adhesion and spreading, it is very likely that more complex responses such as cell differentiation can also be altered within wettability and stiffness variations, hence the importance of also conducting longer term studies with this type of gradient.

Example 6: Fibrotic Response on Topography Gradients

With a view of understanding how topography can influence the fibrotic response as observed when most biomaterials are implanted in the body, Human skin Fibroblasts (HskF) and Lense Epithelial Cells (LEC) were seeded onto two different topography 1 cm-wide gradients—small ranging features and large ranging features. Both cells were stained to allow for the visualization of α-SMA expression, marker that is associated with myofibroblast transition in many body tissues fibrosis [40][41] as well as a fibrotic LEC phenotype [42].

Figure 8A:
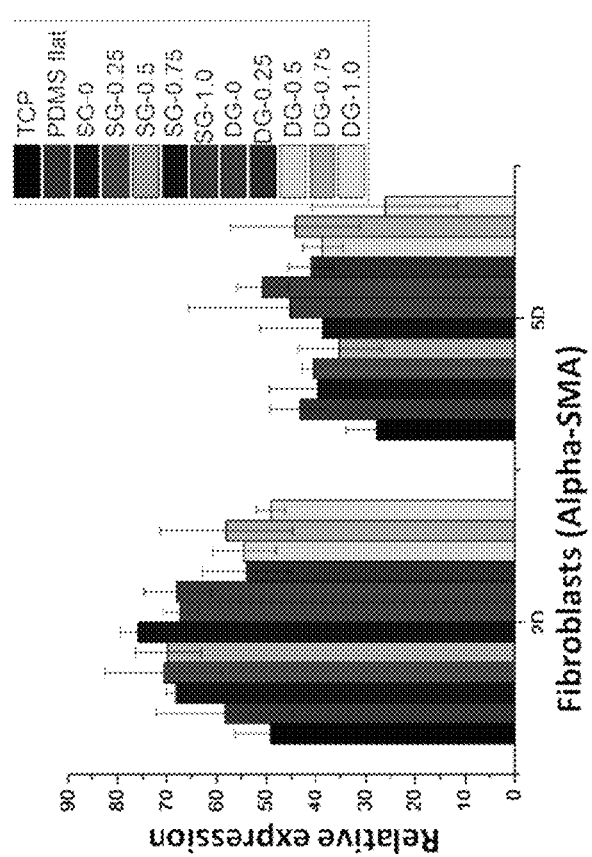
FIG. 8—Fibroblast morphology changes in response to topography gradients and influences Cell Area, Cell Orientation, and Cell Elongation which could be assessed via fluorescence microscopy which also allowed for analysis of the expression of fibrotic markers such as alpha-SMA (A) and Collagen I.(B) S0—Small Feature Gradient, 0 cm; S0,25—Small Feature Gradient, 0.25 cm; S0,5—Small Feature Gradient, 0.5 cm; S0,75 cm—Small Feature Gradient, 0.75 cm; S1—Small Feature Gradient, 1 cm. L0—Large Feature Gradient, 0 cm; L0,25—Large Feature Gradient, 0.25 cm; L0,5—Large Feature Gradient, 0.5 cm; L0, 75 cm—Large Feature Gradient, 0.75 cm; S1—Large Feature Gradient, 1 cm. Statistical analysis done through one-way Anova. ****p<0,0001
Figure 8B:
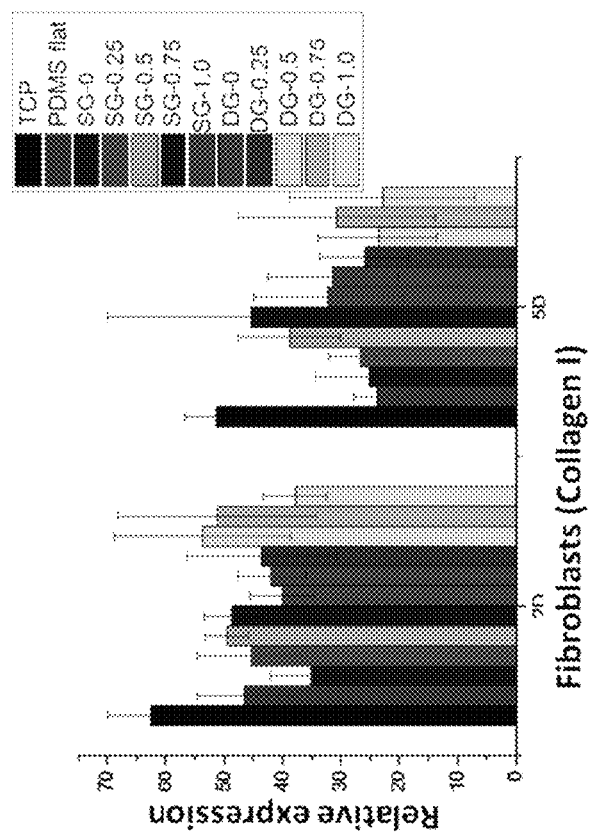

In order to compare the expression of α-SMA in on different positions, cells cultured on the beginning and end of each gradient (data not shown) gradients were analyzed. Both cell types increase the expression of α-SMA when moved onto PDMS surfaces in comparison to when cultured on TCP. As the topography features increase in size, HskF start aligning with the wrinkles, becoming more elongated, as quantified in the graphs of FIG. 8, showing very significant differences between cell morphology in the different portions of the gradient. FIG. 8A displays the response of the fibroblasts with respect to alignment and elongation while protein expression (α-SMA) is highest on the intermediate after two days culture, at five days there is no difference. For collagen I expression (FIG. 8B) this is the opposite where at 5 days culture the intermediate topography displays the highest collagen I production which is regarded as an unfavorable cell response for biomedical implants.

Figure 9:
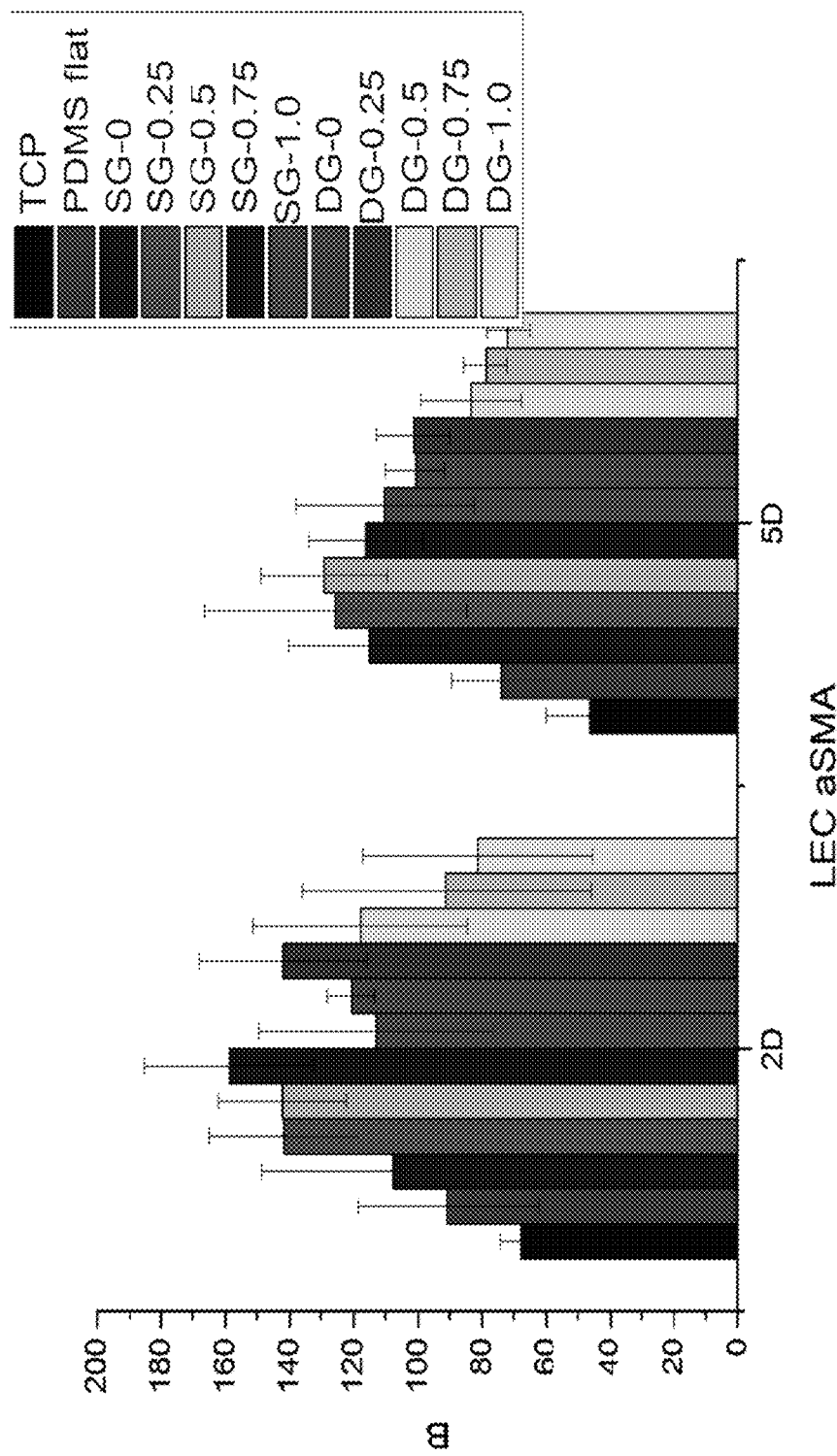
FIG. 9—Lens Epithelial Cell morphology changes in response to topography gradients which was assessed via fluorescence microscopy and also enabled analysis of the expression of fibrotic marker such as alpha-SMA. S0—Small Feature Gradient, 0 cm; S0,25—Small Feature Gradient, 0.25 cm; S0,5—Small Feature Gradient, 0.5 cm; S0.75 cm—Small Feature Gradient, 0.75 cm; S1—Small Feature Gradient, 1 cm. L0—Large Feature Gradient, 0 cm; L0,25—Large Feature Gradient, 0.25 cm; L0,5—Large Feature Gradient, 0.5 cm; L0,75 cm—Large Feature Gradient, 0.75 cm; S1—Large Feature Gradient, 1 cm.
Figure 11A:
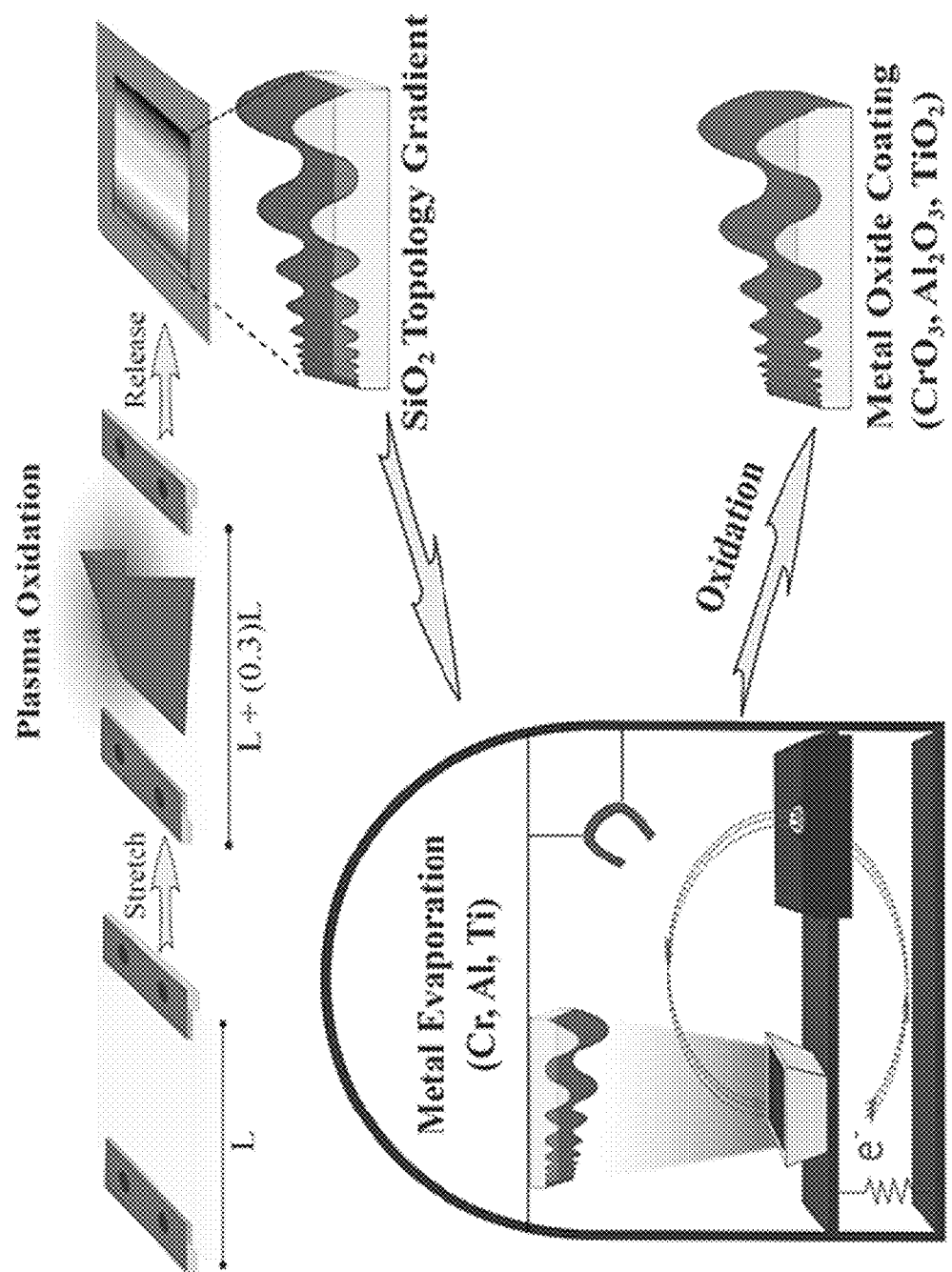
FIG. 11—A) Inorganic aligned topography gradient formation. Schematic illustration of the process to prepare wrinkled gradients with $SiO_2$ via prolonged plasma oxidation and different metal oxide coatings by metal evaporation and exposure to air under ambient conditions. B) XPS spectra of wrinkle gradients with $SiO_2$ and different metal oxide layers. C&D) Dependence of the wavelength and amplitude of created wrinkle gradients with different surface compositions. The 650s surfaces start where the 100s surfaces end with respect to wavelength and amplitude. Data are reported as mean standard deviation (SD) (n=30 wrinkles). Cell response analysis on inorganic biomaterial wrinkle gradient platforms. Macroscopic response of cells toward surface gradients with different interface materials. E) Surface coverage by cells. F) Cell area. G) Cell orientation. H) Cell elongation. (n=150 cells). * indicates that both groups are statistically different (p<0.05). $A_0W_0$(Amplitude 0 nm; Wavelength 0 nm). Focal adhesion analysis on inorganic biomaterial wrinkle gradient platforms. Dependence of focal adhesion area per cell I) and focal adhesion orientation J) on wrinkle gradients with different interface materials, respectively. Data are reported as mean standard deviation (SD) (n=~100 cells). * indicates that both groups are statistically different (p<0.05). A0W0 (Amplitude 0 nm; Wavelength 0 nm).
Figure 11B:
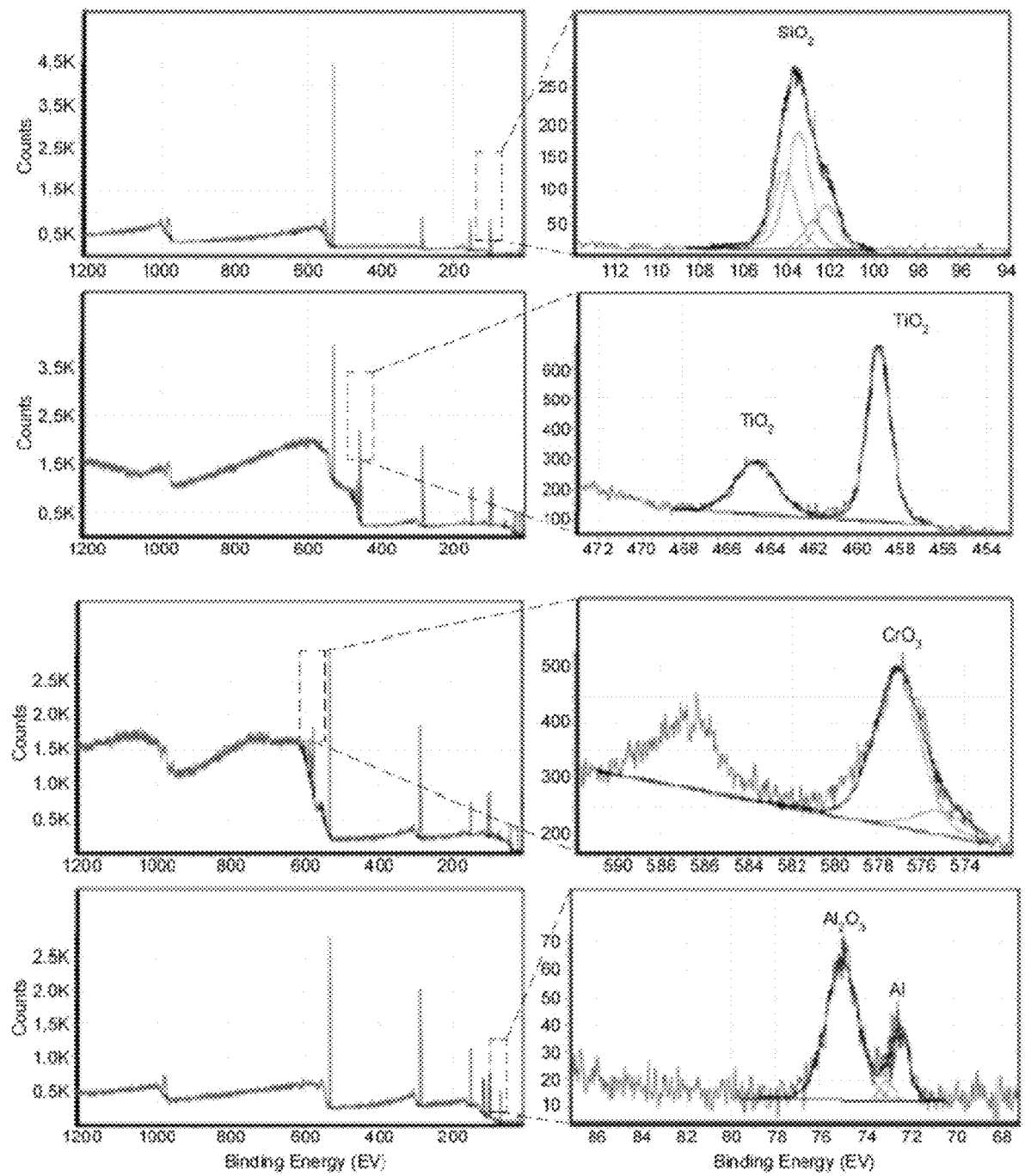
Figure 11C:
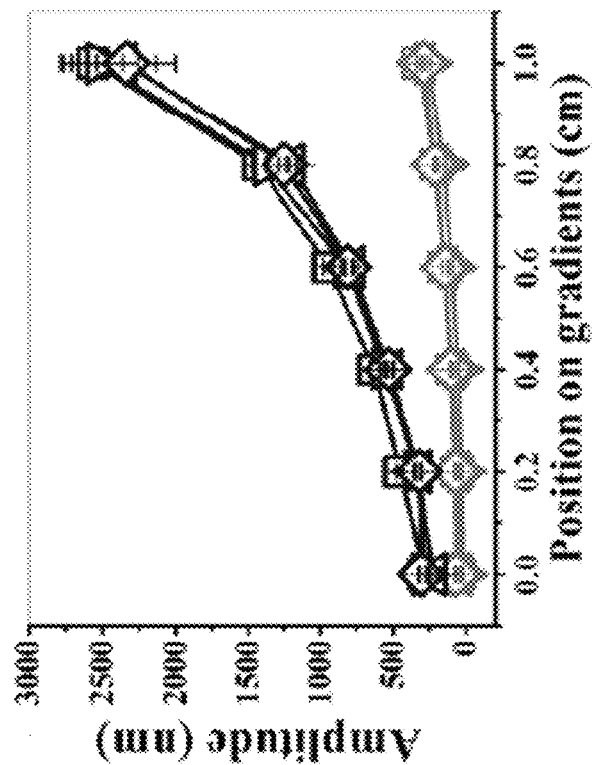
Figure 11D:
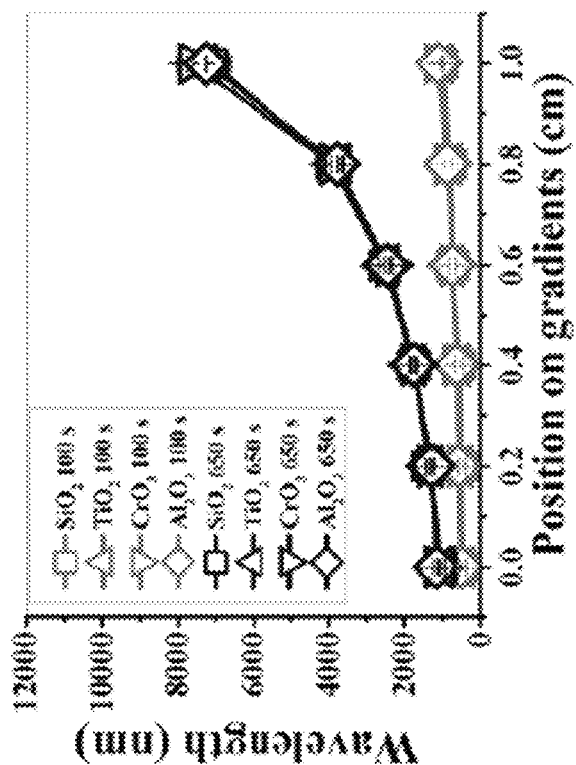

For Lens Epithelial Cells (LECs), it is clearly shown that the orientation and elongation occurs at the largest topography features (FIG. 9). The expression of α-SMA however is most prominent at the lower features and the trend after two days culture is very similar as for five days culture. This indicates that LECs mostly respond negatively to the smaller feature which pushes them more towards a fibrotic state.

Example 7: Towards Optimum Skeletal Muscle Engineering

Satellite cells were successfully proliferated (PM) and differentiated (DM) in nanowrinkled gradients for 12 days. Alignment of satellite cells, myoblast and myotubes was readily achieved and influence of different topographies due to gradient surface was visible in parameters like cell area, cell density, diameter and length. Cell density decreased over time suggesting cell fusion. Thus, cell number decreased but remaining cells had greater areas. However, total cells coverage of the gradient surface was barely different between PM, 6 days DM and 8 days DM. PM showed cell concentration in the middle of the gradient suggesting a preferred wrinkle size for satellite cells of 7 to 12 mm (wavelengths between 3.6 μm and 2.2 μm and heights between 320 nm 800 nm). Whereas 6 days DM showed almost an even distribution across gradient being 0-14 mm preferred positions by cells. Finally, 8 days DM showed most preferred position range between 0 mm to 5 mm. The results obtained indicate that cells are behaving differently according to their maturation stages and are having diverse wrinkle preferences accordingly.

Myoblast and myotube alignment has been widely report in literature but a clear relationship between wrinkle size in a gradient and myotube features (cell area, diameter and length) has not been determined. During this research it was possible to identify that alignment was efficiently induced and that the diameter of the myofibers could be controlled depending on the surface topography. Madden et al. reported that structural maturation of myobundles can be determined by increase in myofiber diameter. Here it was possible to observe that diameter increased from lower wrinkle features to big wrinkle features simultaneously (FIG. 10C displays the controlled morphology which is not obtained with the tissue culture polystyrene standard) showing that no only time but surface topology can affect cell growth.

It was confirmed that during myogenesis process different cell types are present. Analysis of the cell area gave an idea of which cell types (satellite cells, myoblast, myocytes or myotubes) were present on the gradient surfaces. According to the analysis in cell area reported here, differentiated cells with an area larger than 500 um2 had elongated shapes or more than one nucleus and corresponded to 83.7% and 86.3% of the total cell population for 6 d and 8 d respectively. These results agree with the idea that about 80% of satellite cells are entering to cell cycle providing myonuclei to growing fibers and the remaining 20% of the cells divide slowly or entered a quiescent state.

Example 8: Topography Gradients on Clinically Relevant Orthopedic Implant Materials Biomimetic topographical gradients of various clinically relevant inorganic biomaterial interfaces ($SiO_2$, $TiO_2$, $CrO_3$, $Al_2O_3$) were developed via combination of masked plasma-oxidation and metal deposition-oxidation methods to study hBM-MSCs responses in vitro. This high-throughput screening platform correlating with the interfacial properties and biological functions enables systematic study of the topography-biomaterials chemistry cues on cell behavior. It was found that certain features of hBM-MSC behaviors (cell coverage, area, and focal adhesion area per cell) on different interface materials are worse than that on the flat and the micro structured surfaces (FIG. 11). The optimal wrinkle dimension selected here (wavelength: 7121 nm; amplitude: 2561 nm) for promoting hBM-MSCs alignment, cytoskeleton arrangement, long/parallel filopodia as well as focal adhesion assembly and orientation was obtained based on above platforms. In addition, these findings demonstrate that the cellular characteristics are tightly correlated: namely cell alignment has a positive correlation with respect to the orientation of cytoskeleton, filopodia and focal adhesions. The gradient platforms containing both wrinkles and material chemistry can generate synergistic effects on the response of BM-hMSCs, especially surface coverage by cell, cell area, elongation, and the formation of filopodia and focal adhesions, indicating that we need to apply a screening to assess optimum conditions for both current and new biomaterials. While general physical gradients are able to provide insights, when real assessments need to be made, the best way is to use the actual biomaterial in a gradient fashion and screen for the logical parameters, which would provide important information for designing biomaterials and scaffolds used for cell cultivation and tissue engineering.

Although our study focuses on hBM-MSCs behaviors, the developed platform is not limited to this cell type. Future investigations will include various cell types, but also focus on cell function correlated to tissues with known intrinsic anisotropy (e.g. skeletal muscle, blood vessels, neurons etc.) to screen for optimal conditions. Novel biomaterial interfaces have been developed from multiparameter and combinatorial fashions, which often enables complex functions beyond the simple sum of discrete samples. In order to achieve efficiency and complexity, high-throughput approaches are excellent tools, towards establishing property-activity relationships between biointerfaces and biological systems. The combination of a novel HTS approach, advanced imaging, and efficient analysis methods are positioned to accelerate the pace of discovery for next generation materials for biotechnology and medicine.

Example 9: Hard-Soft Translation of Topography Surface Features

Figure 12A:
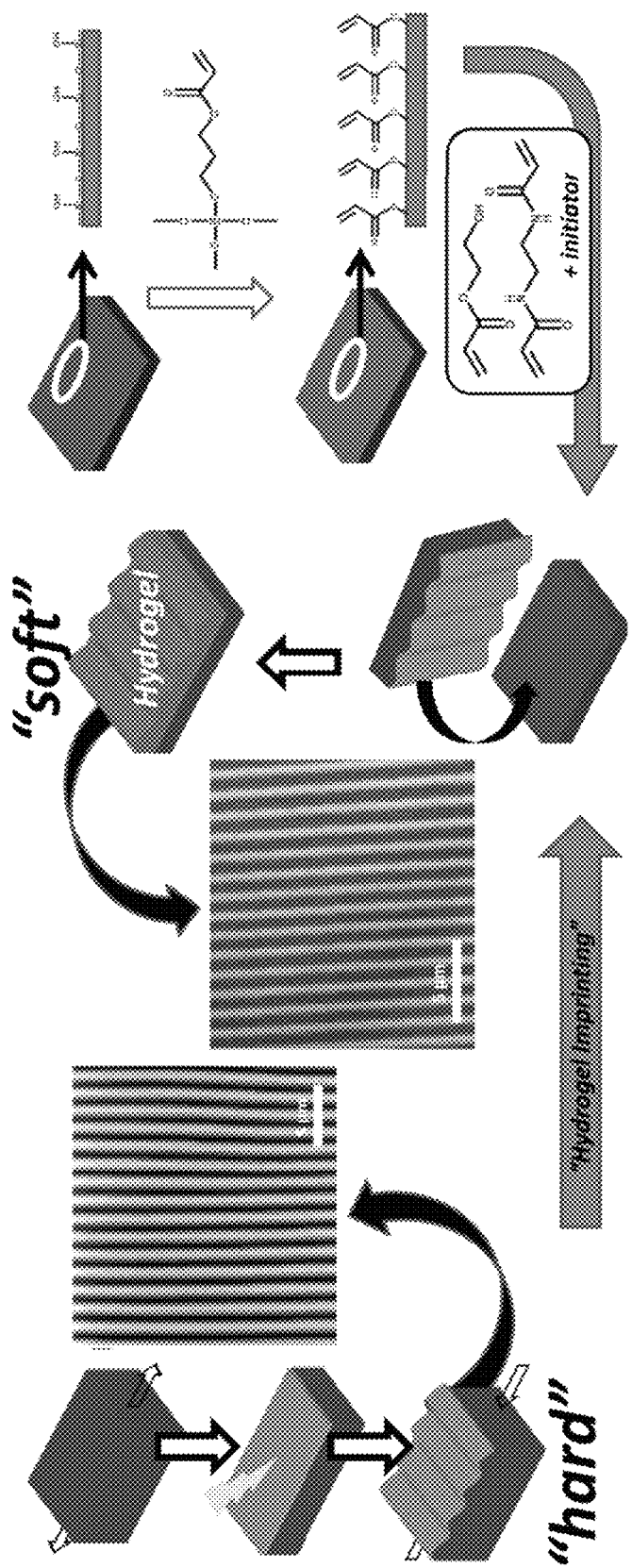
FIG. 12—A) Schematic approach on the preparation of PDMS nanotopological surfaces and the translation of the nanotopology into soft polymeric hydrogel structures via "Hydrogel Nano-Imprinting Lithography". B-D) Viability assay (XTT) displaying the metabolic activity of SaOs (B), HSkF (C) and LEC (D) on soft and hard surfaces both flat and with aligned nanotopology for 2 and 5 days culture. E-G) Macroscopic response of cells (E: SaOs; F: HSkF; G: LEC) towards surface features comparing the wrinkled feature with flat and hard with soft after 2 and 5 days of culturing on the respective surfaces. Cells are considered aligned when cell longitude axis is within 10° of that of the direction of the surface features.

Here we demonstrate the importance of developing materials which enable investigations towards more complex interfaces, in order to elucidate cellular responses towards combined surface properties. For the system development, PDMS (polydimethylsiloxane) substrates and pHEMA (poly (2-hydroxyethyl methacrylate) hydrogels were chosen since both are already used for biomedical applications such as medical implants and contact lenses. Nanostructured PDMS was translated to pHEMA hydrogels, resulting in the same topography but with a different stiffness (FIG. 12A). These property combinations were expected to trigger different cell responses both macroscopically and on a molecular scale (FIG. 12B-G). Aligned nanowrinkles on PDMS substrates were used as the hard topographical substrate. This substrate was also used as the template to prepare hydrogel wrinkles serving as the soft topological substrates with the same features and dimensions. The two different surfaces with similar topography but different stiffness were combined with three human cell-lines, namely osteoblast-like cells (sarcoma osteoblast-like cell-line; SaOs), fibroblasts (skin fibroblast; HSkF) and lens epithelial cells (LEC), to illustrate the different behavior of the cell-types originating from tissues with different intrinsic stiffness. The behavior on structured surfaces was additionally compared to behavior on flat, non-structured surfaces of the same stiffness (planar PDMS and hydrogel). Combining cells from tissues of different intrinsic stiffness with substrata with similar topographies but differing in stiffness, provided insights into specific behavior towards surface topographies. Importantly, it emphasizes the need to combine surface parameters to derive a better understanding of cells at (bio)interfaces.

The wrinkle structures on the surface of PDMS substrates were induced by applying a uni-directional strain with subsequent surface oxidation via oxygen-plasma treatment. The same oxygen plasma treatment in combination with a uni-directional strain induced by a 30% substrate extension followed by release of that strain after the oxidation, induced the formation of surface wrinkles with 255 nm (sd.:11 nm) in amplitude (A) with a wavelength (λ) of 1032 nm (sd.: 57 nm). The wrinkled PDMS is post-treated with oxygen plasma ensuring a homogenous and full surface oxidation omitting any stiffness and chemical inhomogeneity.

For creating soft topologies, imprinting lithography was applied. This is a technique which has been used before to create soft surface confined structures. Wrinkled PDMS was used as a lithographic template.

Imprinting lithography method was performed under inert atmosphere (glove-box) for hydrogels to enhance the degree of polymerization by preventing oxygen-induced termination. Polymerization was performed overnight after which the PDMS substrate was removed. The surface modification of glass with acrylate moieties ensured covalent attachment of the hydrogel layers to the surface enhancing its stability.

It was found that culturing cells of different tissue origin on the different substrates varying in stiffness and topography had a dramatic displaying not only significant deviating response to the surface topography, but also fibrotic markers such as α-SMA and collagen I were highly upregulated when specific combinations of surface parameters were introduced.

Figure 13:
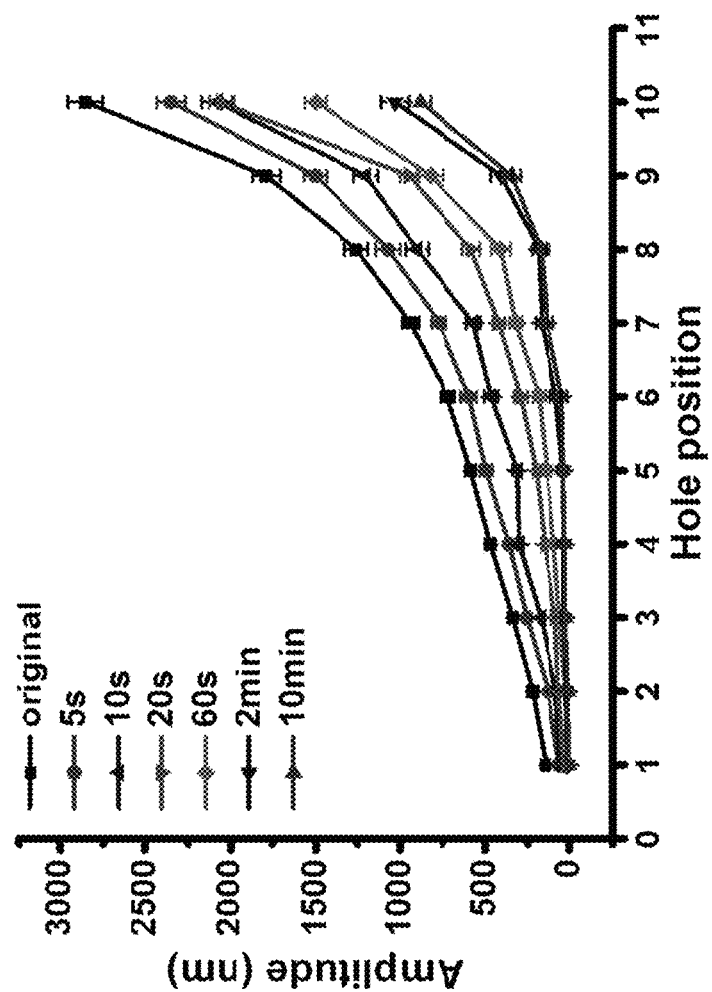
FIG. 13—Graph of the development of amplitude with different plasma oxidation times. Amplitude is reduced with increasing time while the wavelength remains unaltered.
Figure 14:
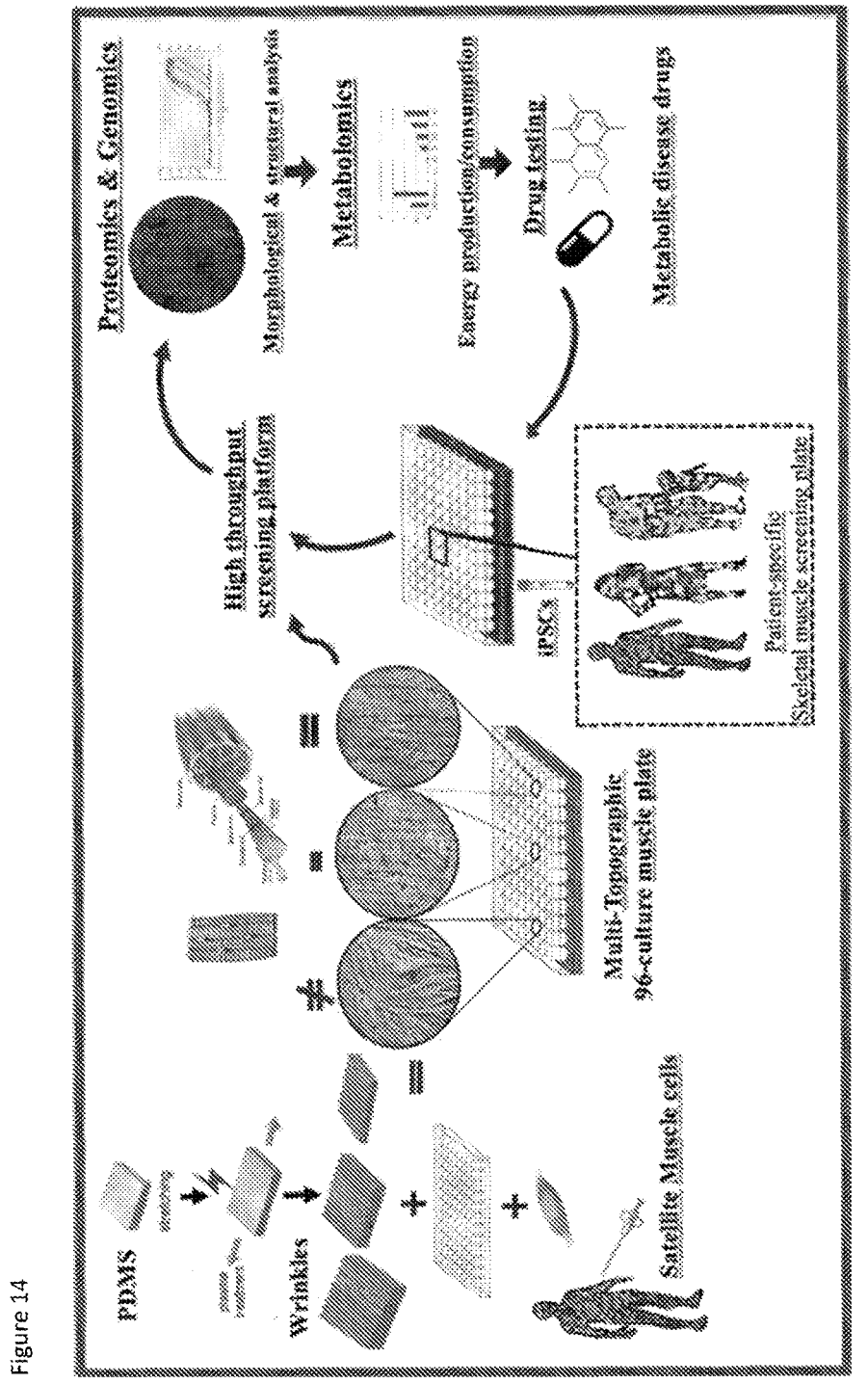
FIG. 14—Integration of PDMS platform into 96-well plate culture systems.

Example 10: Decoupling Amplitude from Wavelength within the Aligned Topography Gradient: Double Orthogonal Topography Arrays The wrinkle gradient PDMS substrate after imprinting was divided into 7 equal areas and plasma treated for different time periods to gradually reduce the amplitude. All the samples were re-imprinted to ensure that surface chemistry as well as stiffness are equal. The wrinkle size increased from the least exposed side (lowest plasma dose) to the most exposed side. The unidirectional gradients were obtained with amplitudes ranging from 144 to 3000 nm and wavelengths between 700 and 14000 nm. After different oxidation times, 7 kinds of different amplitudes were obtained, the value corresponding to 144 nm decreased to 6 nm and 3000 nm decreased to 800 nm. (FIG. 13).

Example 11: Platform Integration into Standardized Cell Culture Plates as for High-Throughtput Screening of Muscle Tissue After samples were measured, each section of PDMS was cut according to the required rectangle size for embedding in a 96-well plate (Control, 7 um and 9 um sections in 2.4×7.5 cm; 1 um and 2 um in 2.7×7.5 cm; 4 um and 6 um in 3.6×7.5 cm). They were placed on top of a bottomless 96-well plate (Greiner BioKOne, no. 82051K526) as described in the diagram (FIG. 1) to ensure alignment. The bottom of another bottomless 96-well plate was coated using an even distribution of ~1.7 g of PDMS mix, which was applied using a syringe (Eppendorf Combitips Advanced®, 5.0 mL cat. no. 0030089456) in an "S" motion following the edge and spread out to cover the surface crossing over all junctions of the bottom.

Once the bottom of the plate was covered, it was cured in an oven (preheated at 70° C.) for 8 min. ensuring a balance in viscoelasticity, one that allowed for the wrinkle sheets to bond with the plate, but not the new gluing PDMS to spread into the well area. If consistency was not yet achieved at this time, 1 or 2 minutes of extra oven time was allowed. Once the desired viscosity was obtained, the plate was quickly removed from the oven and placed on top of the prepared wrinkle substrates set on the 96 well plate in order to align and match all 4 corners. The plate "sandwich" was flipped and the one holding the wrinkles on its bottom was detached gently. Low pressure was applied to the junction points in order to ensure complete sealing of each well, after which, it was placed back in the oven at 70° C. for 20 minutes with an extra plate set on top of the bottom of the plate together with 4.5 kg to apply an even pressure while curing.

As all wrinkle substrates were coupled with the plate, we checked for any leakage or communication between wells in a twoKstep way, first by adding 200 μL of demiKwater in a checkerKboard pattern, and secondly, by filling all wells with water and pipetting to create a flow in case of small communications. Finally, after checking for coupling quality, we proceeded to seal the bottom of the plate with ~30 g of PDMS mix by pouring first into the edges and finally on top of the wrinkle substrates spread evenly. Plate was cured for 3 hrs at 70° C. In order to sterilize the plates for cell culture, wells were sprayed with ethanol 70% and brought into the flow chamber. They were washed one time with 300 μL of PBS, then 300 μL of ethanol 70% and a last wash with 300 μL PBS after which they were covered with their lid and put in the incubator to dry and be later bagged to await cell seeding. A cell culture to create muscle tissue mimics was performed as described in Example 7.

REFERENCES

[1] HUBBELL, Jeffrey A. Biomaterials in tissue engineering. Bio/technology (Nature Publishing Company), 1995, 13.6: 565-576.

[2] LUTOLF, M. P.; HUBBELL, J. A. Synthetic biomaterials as instructive extracellular microenvironments for morphogenesis in tissue engineering. Nature biotechnology, 2005, 23.1: 47-55. [3] TIBBITT, Mark W.; ANSETH, Kristi S. Hydrogels as extracellular matrix mimics for 3D cell culture. Biotechnology and bioengineering, 2009, 103.4: 655-663.

[4] NEL, Andre E., et al. Understanding biophysicochemical interactions at the nano-bio interface. Nature materials, 2009, 8.7: 543-557.

[5] RUOSLAHTI, Erkki; PIERSCHBACHER, Michael D. New perspectives in cell adhesion: RGD and integrins. Science, 1987, 238.4826: 491-497.

[6] LAMPIN, M., et al. Correlation between substratum roughness and wettability, cell adhesion, and cell migration. Journal of biomedical materials research, 1997, 36.1: 99-108.

[7] ARIMA, Yusuke; IWATA, Hiroo. Effect of wettability and surface functional groups on protein adsorption and cell adhesion using well-defined mixed self-assembled monolayers. Biomaterials, 2007, 28.20: 3074-3082.

[8] JAALOUK, Diana E.; LAMMERDING, Jan. Mechanotransduction gone awry. Nature reviews Molecular cell biology, 2009, 10.1: 63-73.

[9] DISCHER, Dennis E.; JANMEY, Paul; WANG, Yu-li. Tissue cells feel and respond to the stiffness of their substrate. Science, 2005, 310.5751: 1139-1143.

[10] Shih, Yu-Ru V., et al. "Matrix stiffness regulation of integrin-mediated mechanotransduction during osteogenic differentiation of human mesenchymal stem cells." Journal of Bone and Mineral Research 26.4 (2011): 730-738.

[11] BETTINGER, Christopher J.; LANGER, Robert BORENSTEIN, Jeffrey T. Engineering substrate topography at the micro- and nanoscale to control cell function. Angewandte Chemie International Edition, 2009, 48.30: 5406-5415.

[12] Falconnet, Didier, et al. "Surface engineering approaches to micropattern surfaces for cell-based assays." Biomaterials 27.16 (2006): 3044-3063.

[13] VOGEL, Viola; SHEETZ, Michael. Local force and geometry sensing regulate cell functions. Nature reviews Molecular cell biology, 2006, 7.4: 265-275.

[14] GHAEMI, Soraya Rasi, et al. Exploring the mesenchymal stem cell niche using high throughput screening. Biomaterials, 2013, 34.31: 7601-7615.

[15] DI LUCA, Andrea, et al. Influencing chondrogenic differentiation of human mesenchymal stromal cells in scaffolds displaying a structural gradient in pore size. Acta biomaterialia, 2016, 36: 210-219.

[16] WANG, Peng-Yuan, et al. Screening mesenchymal stem cell attachment and differentiation on porous silicon gradients. Advanced Functional Materials, 2012, 22.16: 3414-3423.

[17] VINCENT, Ludovic G., et al. Mesenchymal stem cell durotaxis depends on substrate stiffness gradient strength. Biotechnology journal, 2013, 8.4: 472-484.

[18] FAIA-TORRES, Ana B., et al. Differential regulation of osteogenic differentiation of stem cells on surface roughness gradients. Biomaterials, 2014, 35.33: 9023-9032.

[19] M A, Yanrui, et al. Concentration-Dependent h MSC Differentiation on Orthogonal Concentration Gradients of GRGDS and BMP-2 Peptides. Biomacromolecules, 2016, 17.4: 1486-1495.

[20] PETERSON, Sophie L., et al. Poly (dimethylsiloxane) thin films as biocompatible coatings for microfluidic devices: cell culture and flow studies with glial cells. Journal of Biomedical Materials Research Part A, 2005, 72.1: 10-18.

[21] KIM, Sung Hwan, et al. Flexible, stretchable and implantable PDMS encapsulated cable for implantable medical device. Biomedical Engineering Letters, 2011, 1.3: 199-203.

[22] TSEREPI, Angeliki, et al. Tailoring the surface topography and wetting properties of oxygen-plasma treated polydimethylsiloxane. Journal of applied physics, 2005, 98.11: 113502.

[23] BÉFAHY, Stéphane, et al. Thickness and elastic modulus of plasma treated PDMS silica-like surface layer. Langmuir, 2009, 26.5: 3372-3375.

[24] VLACHOPOULOU, M.-E., et al. Effect of surface nanostructuring of PDMS on wetting properties, hydrophobic recovery and protein adsorption. Microelectronic Engineering, 2009, 86.4: 1321-1324.

[25] ZHOU Q, Khn P T, Huisman T, et al. Directional nanotopographic gradients: a high-throughput screening platform for cell contact guidance. Scientific Reports. 2015; 5:16240. doi:10.1038/srep16240.

[26] KUHN, Philipp T., et al. Double Linear Gradient Biointerfaces for Determining Two-Parameter Dependent Stem Cell Behavior. ChemNanoMat, 2016, 2.5: 407-413.

[27] MCNAMARA, Laura E., et al. Nanotopographical control of stem cell differentiation. Journal of tissue engineering, 2010, 1.1: 120623.

[28] ARIMA, Yusuke; IWATA, Hiroo. Effect of wettability and surface functional groups on protein adsorption and cell adhesion using well-defined mixed self-assembled monolayers. Biomaterials, 2007, 28.20: 3074-3082.

[29] LAMPIN, M., et al. Correlation between substratum roughness and wettability, cell adhesion, and cell migration. Journal of biomedical materials research, 1997, 36.1: 99-108.
[30] BUTCHER, Darci T.; ALLISTON, Tamara; WEAVER, Valerie M. A tense situation: forcing tumour progression. Nature Reviews Cancer, 2009, 9.2: 108-122.
[31] HOU, Fu J., et al. Human vertebral body apparent and hard tissue stiffness. Journal of biomechanics, 1998, 31.11: 1009-1015.
[32] HAO, Jin, et al. Mechanobiology of mesenchymal stem cells: perspective into mechanical induction of MSC fate. Acta biomaterialia, 2015, 20: 1-9.
[33] WATT, Fiona M.: HUCK, Wilhelm TS. Role of the extracellular matrix in regulating stem cell fate. Nature reviews Molecular cell biology, 2013, 14.8: 467-473.
[34] FRITZ, Jennifer L.; OWEN, Michael J. Hydrophobic recovery of plasma-treated polydimethylsiloxane. The Journal of Adhesion, 1995, 54.1-4: 33-45.
[35] GUPTA, Siddhi, et al. Stiffness- and wettability-dependent myoblast cell compatibility of transparent poly (vinyl alcohol) hydrogels. Journal of Biomedical Materials Research Part B: Applied Biomaterials, 2013, 101.2: 346-354.
[36] DAI, Xiaohan, et al. Synergistic effects of elastic modulus and surface topography of Ti-based implants on early osseointegration. RSC Advances, 2016, 6.49: 43685-43696.
[37] WENG, Shinuo; FU, Jianping. Synergistic regulation of cell function by matrix rigidity and adhesive pattern. Biomaterials, 2011, 32.36: 9584-9593.
[38] SEO, Ji-Hun; SAKAI, Keiko; YUI, Nobuhiko. Adsorption state of fibronectin on poly (dimethylsiloxane) surfaces with varied stiffness can dominate adhesion density of fibroblasts. Acta biomaterialia, 2013, 9.3: 5493-5501.
[39] KESSLER, Felipe, et al. Wettability and cell spreading enhancement in poly (sulfone) and polyurethane surfaces by UV-assisted treatment for tissue engineering purposes. Tissue Engineering and Regenerative Medicine, 2014, 11.1: 23-31.
[40] BRENNER, David A., et al. Origin of myofibroblasts in liver fibrosis. Fibrogenesis & tissue repair, 2012, 5.1: 1.
[41] LEBLEU, Valerie S., et al. Origin and function of myofibroblasts in kidney fibrosis. Nature medicine, 2013, 19.8: 1047-1053.
[42] RAGHAVAN, Cibin T., et al. AGEs in human lens capsule promote the TGF62-mediated EMT of lens epithelial cells: implications for age-associated fibrosis. Aging cell, 2016.
[43] OBERRINGER, Martin, et al. Reduced myofibroblast differentiation on femtosecond laser treated 316LS stainless steel. Materials Science and Engineering: C, 2013, 33.2: 901-908.
[44] KENDALL, Ryan T.; FEGHALI-BOSTWICK, Carol A. Fibroblasts in fibrosis: novel roles and mediators. Frontiers in pharmacology, 2014, 5: 123.
[45] RAJNICEK, Ann M.; FOUBISTER, Louise E.; MCCAIG, Cohn D. Alignment of corneal and lens epithelial cells by co-operative effects of substratum topography and DC electric fields. Biomaterials, 2008, 29.13: 2082-2095.

The invention claimed is:

1. A cell culture system comprising:
a biomaterial substrate formed from a biomaterial,
the biomaterial substrate further including at least a first linear surface gradient oriented orthogonally to a second linear surface gradient, wherein said first gradient and said second gradient are distinct and selected from the group consisting of stiffness (S), topography (T) and wettability (W), and
wherein the at least first linear surface gradient and the second linear surface gradient are both formed from the same biomaterial used for the biomaterial substrate, wherein said biomaterial substrate is formed from a polymer, a biodegradable polymer, a metal or a ceramic material.

2. The system according to claim 1, wherein said S gradient comprises a Young's modulus of from 4 kPa to 100 MPa.

3. The system according to claim 1, wherein said T gradient comprises surface features of 0-20 μm.

4. The system according to claim 1, wherein said W gradient comprises a water contact angle of 20 to 110°.

5. The system according to claim 1, wherein said polymer is an FDA-approved polymer, optionally selected from the group consisting of PDMS, PLA, PGA, PGLA, PCL, PTMC, acrylate-based polymers including PMMA, PNIPAAm, PAA, PHEMA, and Polyethyleneglycol-based acrylates.

6. The system according to claim 1, wherein said biomaterial substrate is a metal, optionally selected from the group consisting of Ti, TiO2, Cr/CrO3, Al/Al2O3, Au and Ni.

7. The system according to claim 1, wherein said biomaterial substrate is a ceramic material.

8. The system according to claim 1, comprising a S gradient oriented orthogonally to a W gradient (S/W).

9. The system according to claim 1, comprising a T gradient oriented orthogonally to a S gradient (T/S).

10. The system according to claim 1, comprising a T gradient oriented orthogonally to a double linear WS gradient (T/WS).

11. The system according to claim 1, further comprising at least one additional surface gradient being a chemical gradient, a porosity gradient, a pore-size gradient, a biological gradient or a viscoelastic gradient.

12. A cell screening platform comprising a combination of at least two distinct cell culture systems according to claim 1.

13. The cell screening platform according to claim 12, further comprising a system comprising a T gradient oriented orthogonally to a W gradient (T/W).

14. A method for providing a cell culture system according to claim 1, comprising providing a biomaterial substrate and applying to said substrate at least a first linear surface gradient oriented orthogonally to a second linear surface gradient.

15. The method for studying cellular function, comprising the steps of
(a) providing a cell culture system according to claim 1;
(b) seeding viable cells on at least part of the surface of the polymer substrate; and
(c) determining the correlation of at least one cellular or biological parameter with at least two biomaterial properties selected from stiffness (S), aligned topography (T) and wettability (W).

16. The method according to claim 15, wherein said cells are
a) mammalian cells, optionally human cells, selected from the group consisting of skin fibroblasts, macrophages, epithelial cells, stem cells, muscle cells;
b) bacterial cells, selected from *E. coli, S. aureus, P. aeruginosa, Bacillus, Lactobacillus;*
c) yeast cells or plant cells; or
d) co-cultures of cells mentioned under a) and b) and/or c).

17. The method according to claim 15, wherein said cellular or biological parameter comprises adhesion, morphology shape, spreading, orientation, migration, proliferation, contact, differentiation, survival, protein expression, gene expression, and any combination thereof.

* * * * *